United States Patent
Danz et al.

(10) Patent No.: US 12,262,635 B2
(45) Date of Patent: Mar. 25, 2025

(54) ORGANIC MOLECULES FOR USE IN OPTOELECTRONIC DEVICES

(71) Applicant: SAMSUNG DISPLAY CO., LTD., Yongin-si (KR)

(72) Inventors: Michael Danz, Eggenstein-Leopoldshafen (DE); Daniel Zink, Bruchsal (DE)

(73) Assignee: Samsung Display Co., Ltd., Yongin-si (KR)

(*) Notice: Subject to any disclaimer, the term of this patent is extended or adjusted under 35 U.S.C. 154(b) by 415 days.

(21) Appl. No.: 15/740,044

(22) PCT Filed: Jul. 4, 2016

(86) PCT No.: PCT/EP2016/065723
§ 371 (c)(1),
(2) Date: Dec. 27, 2017

(87) PCT Pub. No.: WO2017/005698
PCT Pub. Date: Jan. 12, 2017

(65) Prior Publication Data
US 2018/0198075 A1    Jul. 12, 2018

(30) Foreign Application Priority Data

Jul. 3, 2015 (EP) .................................. 15175358
Dec. 17, 2015 (EP) .................................. 15200813
May 9, 2016 (EP) .................................. 16168821

(51) Int. Cl.
*H10K 85/60*    (2023.01)
*C07D 209/08*    (2006.01)
(Continued)

(52) U.S. Cl.
CPC ....... *H10K 85/6572* (2023.02); *C07D 209/08* (2013.01); *C07D 209/56* (2013.01);
(Continued)

(58) Field of Classification Search
CPC ..... C07D 209/56; C07D 209/86; C09K 11/06
See application file for complete search history.

(56) References Cited

U.S. PATENT DOCUMENTS 4,186,199 A * 1/1980 Glamkowski ........ C07D 209/08
514/219
9,306,171 B2    4/2016 Mizuki et al.
(Continued)

FOREIGN PATENT DOCUMENTS

JP    2011121948 A    6/2011
JP    2016-130231 A    7/2016
(Continued)

OTHER PUBLICATIONS

Dunlop, H., Tucker, S., Attempts to prepare optically active tervalent nitrogen compounds. Part I. Syntheses of 1 : 9-phenylenecarbazole and derivatives, J Chem Soc., 1939, p. 1945-56. (Year: 1939).*
(Continued)

*Primary Examiner* — Sean M DeGuire
(74) *Attorney, Agent, or Firm* — Womble Bond Dickinson (US) LLP

(57) ABSTRACT

The invention relates to an organic molecule having a structure of the formula I Formula I (Continued)

where
X=CN or CF$_3$;
D=chemical unit having a structure of the formula I-1:

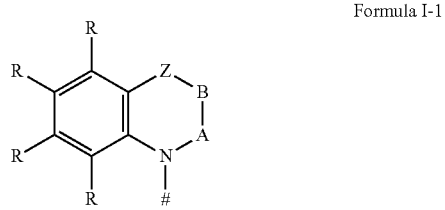

Formula I-1 where
=attachment point of the unit of formula I-1 to the central phenyl ring in the structure of formula I;
A and B=independently of one another are selected from the group consisting of CRR$^1$, CR, NR, N, there being a single or double bond between A and B and a single or double bond between B and Z; and
Z=a direct bond or a divalent organic bridge which is a substituted or unsubstituted C1-C9-alkylene, C2-C8-alkenylene, C2-C8-alkynylene or arylene group or a combination thereof, —CRR$^1$—, —C=CRR$^1$, —C=NR, —NR—, —O—, —SiRR$^1$—, —S—, —S(O)—, —S(O)$_2$—, O-interrupted substituted or unsubstituted C1-C9-alkylene, C2-C8-alkenylene, C2-C8-alkynylene or arylene group, phenyl units or substituted phenyl units.

13 Claims, 11 Drawing Sheets

(51) Int. Cl.

| | | |
|---|---|---|
| C07D 209/56 | (2006.01) | |
| C07D 209/80 | (2006.01) | |
| C07D 209/82 | (2006.01) | |
| C07D 209/86 | (2006.01) | |
| C07D 209/88 | (2006.01) | |
| C07D 215/06 | (2006.01) | |
| C07D 219/08 | (2006.01) | |
| C07D 219/14 | (2006.01) | |
| C07D 241/48 | (2006.01) | |
| C07D 265/38 | (2006.01) | |
| C07D 279/02 | (2006.01) | |
| C07D 279/22 | (2006.01) | |
| C07D 279/26 | (2006.01) | |
| C07D 279/34 | (2006.01) | |
| C07D 403/04 | (2006.01) | |
| C07D 409/10 | (2006.01) | |
| C07D 409/14 | (2006.01) | |
| C07D 417/10 | (2006.01) | |
| C07D 417/14 | (2006.01) | |
| C07D 487/04 | (2006.01) | |
| C07F 7/08 | (2006.01) | |
| C09K 11/06 | (2006.01) | |
| H10K 85/40 | (2023.01) | |
| H10K 50/11 | (2023.01) | |
| H10K 50/12 | (2023.01) | |
| H10K 50/16 | (2023.01) | |
| H10K 50/17 | (2023.01) | |
| H10K 50/18 | (2023.01) | |
| H10K 71/12 | (2023.01) | |
| H10K 71/16 | (2023.01) | |
| H10K 101/30 | (2023.01) | |
| H10K 101/40 | (2023.01) | |

(52) U.S. Cl.
CPC ........ *C07D 209/80* (2013.01); *C07D 209/82* (2013.01); *C07D 209/86* (2013.01); *C07D 209/88* (2013.01); *C07D 215/06* (2013.01); *C07D 219/08* (2013.01); *C07D 219/14* (2013.01); *C07D 241/48* (2013.01); *C07D 265/38* (2013.01); *C07D 279/02* (2013.01); *C07D 279/22* (2013.01); *C07D 279/26* (2013.01); *C07D 279/34* (2013.01); *C07D 403/04* (2013.01); *C07D 409/10* (2013.01); *C07D 409/14* (2013.01); *C07D 417/10* (2013.01); *C07D 417/14* (2013.01); *C07D 487/04* (2013.01); *C07F 7/0816* (2013.01); *C09K 11/06* (2013.01); *H10K 85/40* (2023.02); *H10K 85/615* (2023.02); *H10K 85/636* (2023.02); *H10K 85/655* (2023.02); *H10K 85/657* (2023.02); *C09K 2211/1018* (2013.01); *H10K 50/11* (2023.02); *H10K 50/12* (2023.02); *H10K 50/16* (2023.02); *H10K 50/17* (2023.02); *H10K 50/18* (2023.02); *H10K 71/12* (2023.02); *H10K 71/164* (2023.02); *H10K 2101/30* (2023.02); *H10K 2101/40* (2023.02); *Y02E 10/549* (2013.01); *Y02P 70/50* (2015.11)

(56) References Cited

U.S. PATENT DOCUMENTS

| | | | |
|---|---|---|---|
| 9,647,218 B2 | 5/2017 | Kwong et al. | |
| 10,131,632 B2 | 11/2018 | Lee et al. | |
| 2014/0001446 A1* | 1/2014 | Mizuki | H01L 51/5072 |
| | | | 257/40 |
| 2014/0131686 A1 | 5/2014 | Kawakami et al. | |
| 2016/0072076 A1* | 3/2016 | Stoessel | C07D 219/02 |
| | | | 257/40 |
| 2017/0186973 A1 | 6/2017 | Ren et al. | |
| 2018/0123049 A1 | 5/2018 | Lee et al. | |

FOREIGN PATENT DOCUMENTS

| | | | |
|---|---|---|---|
| KR | 10-2014-0108637 A | 9/2014 | |
| KR | 10-2015-0056046 A | 5/2015 | |
| KR | 10-2016-0116297 A | 10/2016 | |
| KR | 10-2016-0131321 A | 11/2016 | |
| WO | 2014146750 A1 | 9/2014 | |
| WO | 2014146752 A1 | 9/2014 | |
| WO | 2015133353 A | 9/2015 | |
| WO | WO 2016/065724 A1 | 5/2016 | |
| WO | WO-2016111196 A1 * | 7/2016 | ........... C07D 219/14 |
| WO | PCT/EP2016/065723 | 11/2016 | |

OTHER PUBLICATIONS

Mei, L. et al, The inductive-effect of electron withdrawing trifluoromethyl for thermally activated delayed fluorescence: Tunabe emission from tetra-to penta-carbazole in solution processed blue OLEDs, Chem. Commun., Jul. 2, 2015, Royal Society of Chemistry, 51, 13024-13027. (Year: 2015).*
Registry (STN) [online], Oct. 6, 2013 [Searched on Jul. 5, 2019] CAS Reg. No. 1455661-08-1.
Registry (STN) [online], Dec. 11, 2013 [Searched on Jul. 5, 2019] CAS Reg. No. 1492588-48-2.
Registry (STN) [online], Nov. 25, 2013 [Searched on Jul. 5, 2019] CAS Reg. No. 1480291-76-6.
Registry (STN) [online], Dec. 4, 2012 CAS Reg. No. 1410715-53-5.
Registry (STN) [online], Nov. 30, 2012 [Searched on Jul. 5, 2019] CAS Reg. No. 1408611-07-3.

(56) References Cited

OTHER PUBLICATIONS

Registry (STN) [online], Dec. 6, 2012 [Searched on Jul. 5, 2019] CAS Reg. No. 1412417-03-8.
P. Subramanian et al., "A Unified Strategy Towards N-Aryl Heterocycles by a One-Pot Copper-Catalyzed Oxidative C-H Amination of Azoles," European Journal of Organic Chemistry, 2014, pp. 5986-5997, vol. 27.
R.S. Begunov et al., "An interesting recyclization in the course of reduction of 1-(2-nitro-4R-phenyl)-1H-benzimidoles with thin(II) chloride," Mendeleev Communications, 2013, pp. 354-355, 23(6).
E.J. Glamkowski et al., "Synthesis of 1, 2-dihydroindolo [1, 7-ab][1,5]benzodiazepines and related structures (1). A new heterocyclic ring system," Journal of Heterocyclic Chemistry 1979, pp. 865-869, 16(5).
A.C. Geale, "Attempted synthesis of 1,9-9', 1'dicarbazolylene," Journal of Chemical Society, 1956, pp. 1124-1127.
H.G. Dunlop et al., "Attempts to prepare optically active trivalent nitrogen compounds, Part I. Syntheses of 1,9-phenylenecarbazole and derivatives," Journal of the Chemical Society, 1939, pp. 1945-1956.
S. Gong et al., "Simple CBP Isomers with High Triplet Energies for Highly Efficient Blue Electrophosphorescence," Journal of Materials Chemistry, Royal Society of Chemistry, Jan. 1, 2012, pp. 2894-2899, vol. 22, No. 7.
Madadi, Nikhil Reeddy et al. "Synthesis and anti-proliferative activity of aromatic substituted 5-((1-benzyl-1H-indol-3-yl)methylene)-1,3-dimethylpyrimidine-2,4,6(1H,3H,5H)-trione analogs against human tumor cell lines," Bioorganic & Medicinal Chemistry Letters, Dec. 9, 2013, pp. 601-603, vol. 24.
STN Registry, CAS No. 855180-26-6 (2005), 1pg.

\* cited by examiner

ORGANIC MOLECULES FOR USE IN OPTOELECTRONIC DEVICES

CROSS-REFERENCE TO RELATED APPLICATIONS

This application claims priority to International Application No. PCT/EP2016/065723, filed Jul. 4, 2016, which claims priority to European Patent Application No. 15175358.9 filed Jul. 3, 2015 and European Patent Application No. 15200813.2 filed Dec. 17, 2015, and European Patent Application No. 16168821.3 filed May 9, 2016, the disclosures of which are incorporated by reference herein in their entireties.

Field of Invention

The invention relates to purely organic molecules and to the use thereof in organic light-emitting diodes (OLEDs) and in other organic optoelectronic devices.

BACKGROUND

A feature or organic optoelectronic devices is either that electrical energy is converted into photons (organic light-emitting diodes, OLEDs, or light-emitting electrochemical cells, LEECs) or that the opposite process occurs (organic photovoltaics, OPVs). It is important here that these processes run as efficiently as possible. For the sector of OLEDs, therefore, it is necessary ideally to use materials having maximum photoluminescent quantum yield. Limited efficiencies in OLED materials can be improved by using efficient materials which exhibit thermally activated delayed fluorescence (TADF), since, in contrast to purely fluorescent materials, up to 100% of the excitons, rather than 25% of the excitons formed in an OLED, can be utilized. The triplet excitons formed can also in this case be converted into singlet excitons, a state from which photons can then be emitted. A precondition for such thermal repopulation is a low energetic distance between the lowest excited singlet level ($S_1$) and triplet level ($T_1$). This may be achieved, for example, through use of copper(I) complexes (in this regard see, for example: H. Yersin, U. Monkowius, T. Fischer, T. Hofbeck, WO 2010/149748 A1) or else by means of purely organic materials (in this regard see, for example: Q. Zhang et al., *J. Am. Chem. Soc.* 2012, 134, 14706, WO 2013161437 A1).

There is also a large demand for new materials, as for example for deep-blue TADF OLEDs. Existing blue TADF materials often exhibit high exciton lifetimes, which are bad for efficient and long-lived OLEDs. Besides the aforementioned properties of the materials, their availability is also relevant with regard to commercialization. This includes the availability of synthesis building blocks, and also the cost and convenience of the actual synthesis of the functional material, particularly including the purification of this material.

BRIEF DESCRIPTION OF THE DRAWINGS

Exemplary embodiments of the present invention will be described below in more detail, with reference to the accompanying drawings, of which.

Figure 1:
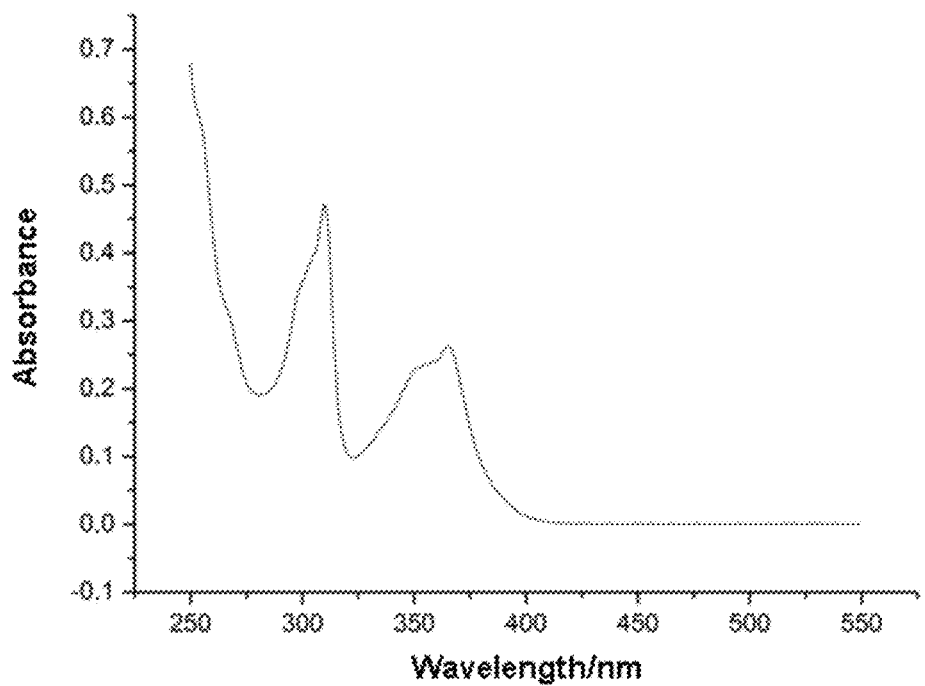
FIG. 1 is an absorption spectrum of 1 as a solution in 2-methyltetrahydrofuran.

Detailed Description of Exemplary Embodiments of the Invention

Exemplary embodiments of the invention will now be discussed in further detail. This invention may, however, be embodied in many different forms and should not be construed as limited to the embodiments set forth herein.

The invention provides a new class of molecules which comprises a structure of the formula I or consist of a structure of the formula I:

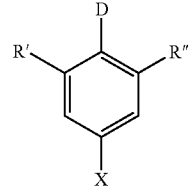

Formula I where
X= an electron-withdrawing unit, in particular CN or $CF_3$;
D= chemical unit having a structure of the formula I-1:

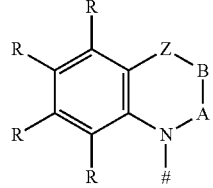

Formula I-1 where
- #= attachment point of the unit of formula I-1 to the central phenyl ring in the structure of formula I;
- A and B= independently of one another selected from the group consisting of $CRR^1$, CR, NR, N, there being a single or double bond between A and B and a single or double bond between B and Z;
- Z= a direct bond or a divalent organic bridge which is a substituted or unsubstituted C1-C9-alkylene, C2-C8-alkenylene, C2-C8-alkynylene or arylene group or a combination thereof, $—CRR^1$, $—C=CRR^1$, $—C=NR$, $—NR—$, $—O—$, $—SiRR^1—$, $—S—$, $—S(O)—$, $—S(O)_2—$, O-interrupted substituted or unsubstituted C1-C9-alkylene, C2-C8-alkenylene, C2-C8-alkynylene or arylene group, phenyl units or substituted phenyl units;
- where each R and $R^1$, identically or differently at each occurrence, is H, deuterium, azide ($N_3^-$), F, Cl, Br, I, $N(R^2)_2$, CN, $CF_3$, $NO_2$, OH, COOH, $COOR^2$, $CO(NR^2)_2$, $Si(R^2)_3$, $B(OR^2)_2$, $C(=O)R^2$, $P(=O)(R^2)_2$, $S(=O)R^2$, $S(=O)_2R^2$, $OSO_2R^2$, a linear alkyl, alkoxy or thioalkoxy group having 1 to 40 C atoms or a linear alkenyl or alkynyl group having 2 to 40 C atoms or a branched or cyclic alkyl, alkenyl, alkynyl, alkoxy or thioalkoxy group having 3 to 40 C atoms, which in each case may be substituted by one or more radicals $R^2$, it being possible for one or more non-adjacent $CH_2$ groups to be replaced by $R^2C=CR^2$, $C≡C$, $Si(R^2)_2$, $Ge(R^2)_2$, $Sn(R^2)_2$, $C=O$, $C=S$, $C=Se$, $C=NR^2$, $P(=O)(R^2)$, SO, $SO_2$, $NR^2$, O, S or $CONR^2$, and it being possible for one or more H atoms to be replaced by deuterium, F, Cl, Br, I, CN, $CF_3$ or $NO_2$, or is an aromatic or heteroaromatic ring system having 5 to 60 aromatic ring atoms, it being possible for this ring system to be substituted in each case by one or more radicals $R^2$, or is an aryloxy or heteroaryloxy group having 5 to 60 aromatic ring atoms, it being possible for this group to be substituted by one or more radicals $R^2$, or is a diarylamino group, diheteroarylamino group or arylheteroarylamino group having 10 to 40 aromatic ring atoms, it being possible for this group to be substituted by one or more radicals $R^2$, or is a combination of these systems, or is a crosslinkable unit QE which may be crosslinked by acid-catalytic, thermal or UV crosslinking methods in the presence or absence of a photoinitiator or by microwave radiation; two or more of these substituents R and $R^1$ may form with one another a mono- or polycyclic, aliphatic, aromatic and/or benzo-fused ring system;
- $R^2$, identically or differently at each occurrence, is H, deuterium, F, Cl, Br, I, $N(R^3)_2$, CN, $CF_3$, $NO_2$, OH, COOH, $COOR^3$, $CO(NR^3)_2$, $Si(R^3)_3$, $B(OR^3)_2$, $C(=O)R^3$, $P(=O)(R^3)_2$, $S(=O)R^3$, $S(=O)_2R^3$, $OSO_2R^3$, a linear alkyl, alkoxy or thioalkoxy group having 1 to 40 C atoms or a linear alkenyl or alkynyl group having 2 to 40 C atoms or a branched or cyclic alkyl, alkenyl, alkynyl, alkoxy or thioalkoxy group having 3 to 40 C atoms, which may be substituted in each case by one or more radicals $R^3$, it being possible for one or more non-adjacent $CH_2$ groups to be replaced by $R^3C=CR^3$, $C≡C$, $Si(R^3)_2$, $Ge(R^3)_2$, $Sn(R^3)_2$, $C=O$, $C=S$, $C=Se$, $C=NR^3$, $P(=O)(R^3)$, SO, $SO_2$, $NR^3$, O, S or $CONR^3$, and it being possible for one or more H atoms to be replaced by deuterium, F, Cl, Br, I, CN, $CF_3$ or $NO_2$, or is an aromatic or heteroaromatic ring system having 5 to 60 aromatic ring atoms, it being possible for this system to be substituted in each case by one or more radicals $R^3$, or is an aryloxy or heteroaryloxy group having 5 to 60 aromatic ring atoms, it being possible for this group to be substituted by one or more radicals $R^3$, or is a diarylamino group, diheteroarylamino group or arylheteroarylamino group having 10 to 40 aromatic ring atoms, it being possible for this group to be substituted by one or more radicals $R^3$, or is a combination of these systems; two or more of these substituents $R^2$ may form with one another a mono- or polycyclic, aliphatic, aromatic and/or benzo-fused ring system;
- $R^3$, identically or differently at each occurrence, is H, deuterium, F, $CF_3$ or an aliphatic, aromatic and/or heteroaromatic hydrocarbon radical having 1 to 20 C atoms, in which also one or more H atoms may be replaced by F or $CF_3$; two or more substituents $R^3$ may form with one another a mono- or polycyclic, aliphatic ring system;
- R'=selected from the group consisting of H, $N(R^4)_2$, $OR^4$, a linear alkyl or alkoxy group having 1 to 40 C atoms or a branched or cyclic alkyl or alkoxy group having 3 to 40 C atoms, it being possible for this group to be substituted in each case by one or more radicals $R^4$, and an aromatic or heteroaromatic ring system having 5 to 60 aromatic ring atoms, it being possible for this system to be substituted in each case by one or more radicals $R^4$;
- R"=selected from the group consisting of $N(R^4)_2$, $OR^4$, a linear alkyl or alkoxy group having 1 to 40 C atoms or a branched or cyclic alkyl or alkoxy group having 3 to 40 C atoms, it being possible for this group to be substituted in each case by one or more radicals $R^4$, and an aromatic or heteroaromatic ring system having 5 to 60 aromatic ring atoms, it being possible for this system to be substituted in each case by one or more radicals $R^4$;
- $R^4$, identically or differently at each occurrence, is H, deuterium, $N(R^5)_2$, $Si(R^5)_3$, a linear alkyl, alkoxy or thioalkoxy group having 1 to 40 C atoms or a branched or cyclic alkyl, alkoxy or thioalkoxy group having 3 to 40 C atoms, it being possible for this group to be substituted in each case by one or more radicals $R^5$, or is an aromatic or heteroaromatic ring system having 5 to 60 aromatic ring atoms, it being possible for this system to be substituted in each case by one or more radicals $R^5$, or is an aryloxy or heteroaryloxy group having 5 to 60 aromatic ring atoms, it being possible for this group to be substituted by one or more radicals $R^5$, or is a diarylamino group, diheteroarylamino group or arylheteroarylamino group having 10 to 40 aromatic ring atoms, it being possible for this group to be substituted by one or more radicals $R^5$, or is a combination of these systems; two or more of these substituents $R^5$ may also form with one another a mono- or polycyclic, aliphatic, aromatic and/or benzo-fused ring system; $R^5$, identically or differently at each occurrence, is H, deuterium or an aliphatic, aromatic and/or heteroaromatic hydrocarbon radical having 1 to 20 C atoms; two or more substituents $R^5$ may also form with one another a mono- or polycyclic, aliphatic ring system.

In a further embodiment, R' is selected from the group consisting of H, $N(R^4)_2$, $OR^4$, thiophene, a linear alkyl or alkoxy group having 1 to 40 C atoms or a branched or cyclic alkyl or alkoxy group having 3 to 40 C atoms, it being possible for this group to be substituted in each case by one or more radicals $R^4$, and of an aromatic ring system having 5 to 60 aromatic ring atoms, it being possible for this ring system to be substituted by one or more radicals $R^4$, and R" is selected from the group consisting of $N(R^4)_2$, $OR^4$, thiophene, a linear alkyl or alkoxy group having 1 to 40 C atoms or a branched or cyclic alkyl or alkoxy group having 3 to 40 C atoms, it being possible for this group to be substituted in each case by one or more radicals $R^4$, and of an aromatic ring system having 5 to 60 aromatic ring atoms, it being possible for this ring system to be substituted by one or more radicals $R^4$.

An aryl group in the sense of this invention contains 6 to 60 aromatic ring atoms; a heteroaryl group in the sense of this invention contains 5 to 60 aromatic ring atoms, of which at least one represents a heteroatom. The heteroatoms are in particular N, O, and/or S. This is the fundamental definition. If other preferences are stated in the description of the present invention, in relation to the number of aromatic ring atoms or of heteroatoms present, for example, then these apply.

An aryl group or heteroaryl group here, respectively, is a simple aromatic ring, i.e. benzene, or a simple heteroaromatic ring, such as pyridine, pyrimidine or thiophene, or a heteroaromatic polycyclic system, as for example phenanthrene, quinoline or carbazole. A condensed (fused) aromatic or heteroaromatic polycyclic system in the sense of the present patent application consists of two or more simple aromatic and/or heteroaromatic rings which are fused with one another.

An aryl or heteroaryl group, which may be substituted in each case by the radicals stated above and may be linked via any desired positions on the aromatic or heteroaromatic moiety is understood in particular to refer to groups derived from benzene, naphthaline, anthracene, phenanthrene, pyrene, dihydropyrene, chrysene, perylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene; pyrrole, indole, isoindole, carbazole, pyridine, quinoline, isoquinoline, acridine, phenanthridine, benzo-5,6-quinoline, isoquinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,2,3,4-tetrazine, purine, pteridine, indolizine and benzothiadiazole or combinations of these groups.

A cyclic alkyl, alkoxy or thioalkoxy group in the sense of this invention refers to a monocyclic, bicyclic or polycyclic group.

For the purposes of the present invention, a $C_1$- to $C_{40}$-alkyl group, in which individual H atoms or $CH_2$ groups may also be substituted by the groups stated above, refers for example to the radicals methyl, ethyl, n-propyl, i-propyl, cyclopropyl, n-butyl, i-butyl, s-butyl, t-butyl, cyclobutyl, 2-methylbutyl, n-pentyl, s-pentyl, t-pentyl, 2-pentyl, neopentyl, cyclopentyl, n-hexyl, s-hexyl, t-hexyl, 2-hexyl, 3-hexyl, neo-hexyl, cyclohexyl, 1-methylcyclopentyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2.2.2]octyl, 2-bicyclo[2.2.2]octyl, 2-(2,6-dimethyl)octyl, 3-(3,7-dimethyl)octyl, adamantyl, trifluoromethyl, pentafluoroethyl, 2,2,2-trifluoroethyl, 1,1-dimethyl-n-hex-1-yl-, 1,1-dimethyl-n-hept-1-yl-, 1,1-dimethyl-n-oct-1-yl-, 1,1-dimethyl-n-dec-1-yl-, 1,1-dimethyl-n-dodec-1-yl-, 1,1-dimethyl-n-tetradec-1-yl-, 1,1-dimethyl-n-hexadec-1-yl-, 1,1-dimethyl-n-octadec-1-yl-, 1,1-diethyl-n-hex-1-yl-, 1,1-diethyl-n-hept-1-yl-, 1,1-diethyl-n-oct-1-yl-, 1,1-diethyl-n-dec-1-yl-, 1,1-diethyl-n-dodec-1-yl-, 1,1-diethyl-n-tetradec-1-yl-, 1,1-diethyl-n-hexadec-1-yl-, 1,1-diethyl-n-octadec-1-yl-, 1-(n-propyl)-cyclohex-1-yl-, 1-(n-butyl)-cyclohex-1-yl-, 1-(n-hexyl)-cyclohex-1-yl-, 1-(n-octyl)-cyclohex-1-yl- and 1-(n-decyl)-cyclohex-1-yl-. An alkenyl group refers for example to ethenyl, propenyl, butenyl, pentenyl, cyclopentenyl, hexenyl, cyclohexenyl, heptenyl, cycloheptenyl, octenyl, cyclooctenyl or cyclooctadienyl. An alkynyl group refers for example to ethynyl, propynyl, butynyl, pentynyl, hexynyl, heptynyl or octynyl. A $C_1$- to $C_{40}$-alkoxy group refers for example to methoxy, trifluoromethoxy, ethoxy, n-propoxy, i-propoxy, n-butoxy, i-butoxy, s-butoxy, t-butoxy or 2-methylbutoxy.

The chemical unit D in the molecules of the invention has donor properties. The skilled person is aware in principle of what is meant by donor and acceptor properties, respectively. In one embodiment the chemical unit D is electron-donating. It has a +M effect (positive mesomeric effect). In particular, suitable donor substituents have an atom with a free electron pair, such as an N, O or S atom, for example. Preferred in this context are 5-membered ring heteroaryl groups having precisely one ring heteroatom. These heteroaryl groups may also have further aryl groups fused to them. Especially preferred in that context are carbazole groups or carbazole derivates. Further suitable donor substituents are phenoxazine groups or phenoxazine derivatives. In the case of the latter, the oxygen of the phenoxazine may be replaced, for example, by —$CRR^1$—, —$C=CRR^1$, —C=NR, —NR—, —$SiRR^1$—, —S—, —S(O)—, —$S(O)_2$—, O-interrupted substituted or unsubstituted C1-C9-alkylene, C2-C8-alkenylene, C2-C8-alkynylene or arylene group, phenyl units or substituted phenyl units.

In one embodiment, the electron-withdrawing radical X exerts a –M effect (negative mesomeric effect) or a –I effect (negative inductive effect). The radical X, accordingly, is an acceptor substituent. Suitable acceptor substituents are, in particular, cyano groups or $CF_3$.

In ortho-position to the donor on the aromatic moiety, the molecules of the invention have a substituent. This permits effective separation of HOMO and LUMO of the organic molecule.

The molecules of the invention exhibit thermally activated delayed fluorescence and emit in particular in the dark blue region of the visible spectrum.

The use of the molecules of the invention in an optoelectronic device, such as an OLED, leads to higher efficiencies on the part of the device. Furthermore, OLEDs in the dark blue colour spectrum can be realized. Corresponding OLEDs have a greater stability than OLEDs with known emitter materials and of comparable colour.

The crosslinkable units QE comprise in one embodiment a compound selected from the group consisting of oxetanes, alkines and azides, more particularly for a click reaction, and also the following alkene derivatives:

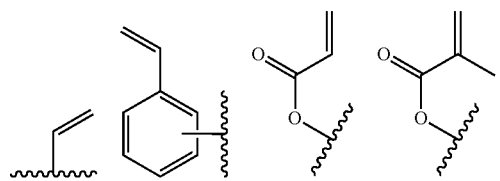

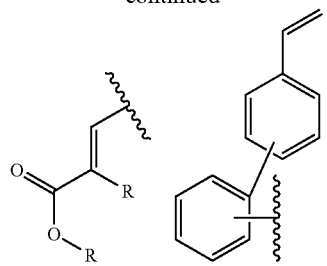

In an alternative embodiment, Z is a covalent single bond or a divalent organic bridge selected from substituted and unsubstituted alkylene (including branched or cyclic), alkenylene, alkynylene, arylene and heteroarylene groups, O, NR, C=CR$_2$, C=NR, SiR$_2$, S, S(O), S(O)$_2$, BR, PR, P(O)R, with combinations of these units also being possible (for example O-interrupted alkylene (including branched or cyclic), alkenylene, alkynylene, arylene and heteroarylene groups).

In one embodiment, D independently of one another is in each case a donor group having electron-donating properties, selected from the group consisting of substituted and unsubstituted carbazole, substituted or unsubstituted indole, substituted and unsubstituted indoline, substituted and unsubstituted dihydroacridine, substituted and unsubstituted benzimidazole, substituted and unsubstituted 2,3,4,9-tetrahydrocarbazole, substituted and unsubstituted 1,2,3,4-tetrahydroquinoline, substituted and unsubstituted phenothiazine, substituted and unsubstituted phenoxazine, substituted and unsubstituted dihydrophenazine, substituted and unsubstituted spiro compounds.

In one embodiment of the organic molecule, the donor group having electron-donating properties of the formula I-1 comprises a structure of the formula II:

Formula II

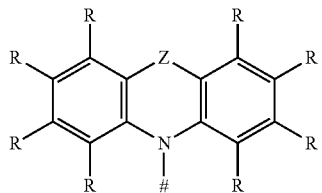

where the definitions of #, Z and R are as stated above in connection with formula I.

The donor group having electron-donating properties of the formula I-1 may in one embodiment comprise a structure of the formula III:

Formula III

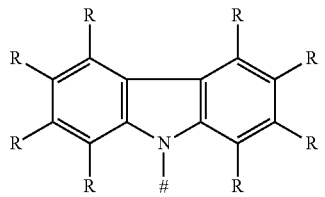

where the definitions of # and R are as stated above in connection with formula I.

Examples of Donors of the Invention:

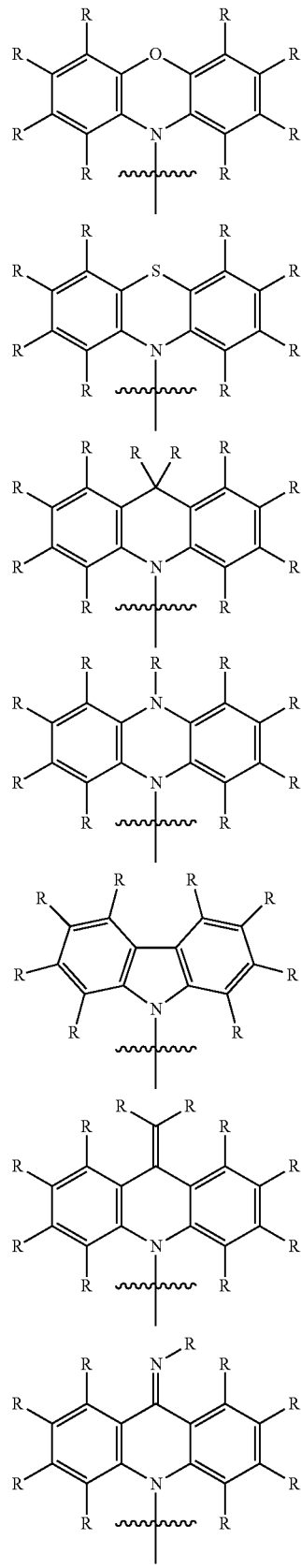

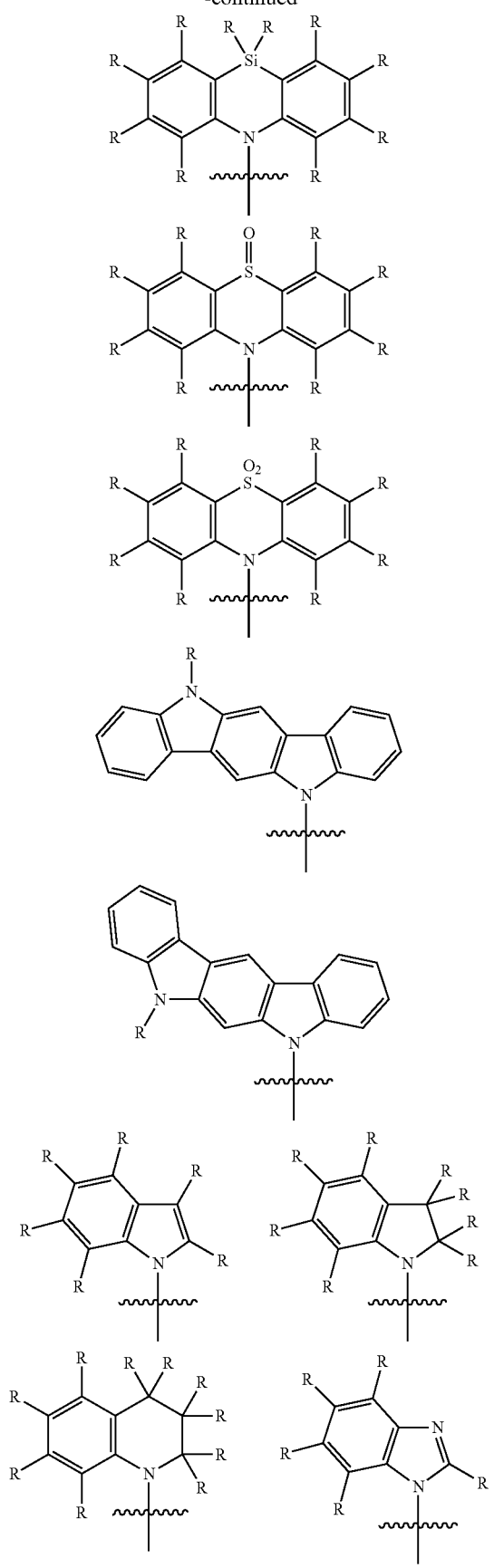
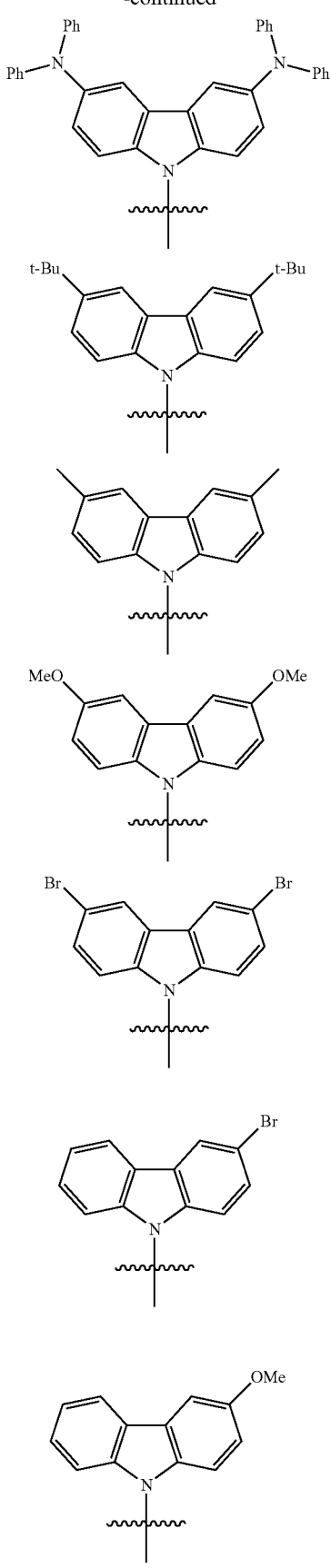

-continued

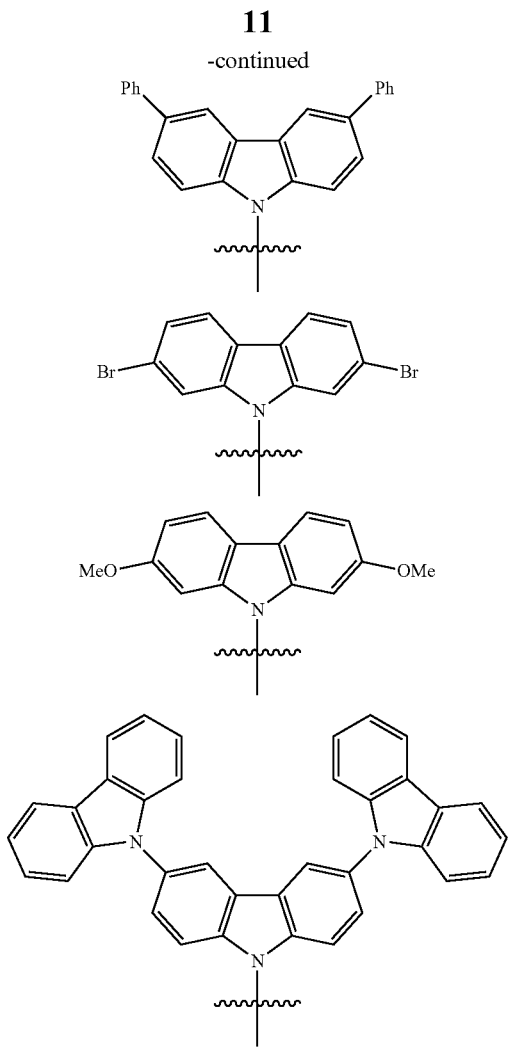

The accepting unit X of the formula I is CN in one embodiment and CF$_3$ in another embodiment. In a further embodiment of the invention, the radical R' of the formula I is a hydrogen atom, i.e. H.

In a further aspect, the invention relates to a process for preparing an organic molecule of the invention, of the type described here (with a possible subsequent reaction).

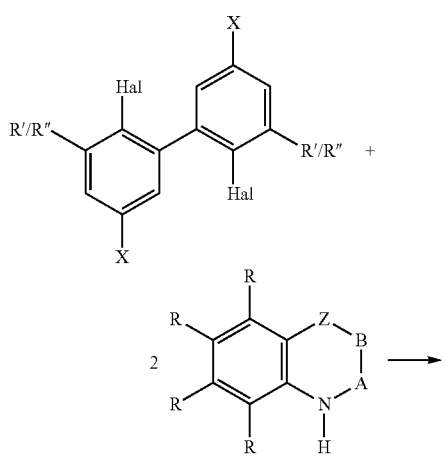

-continued

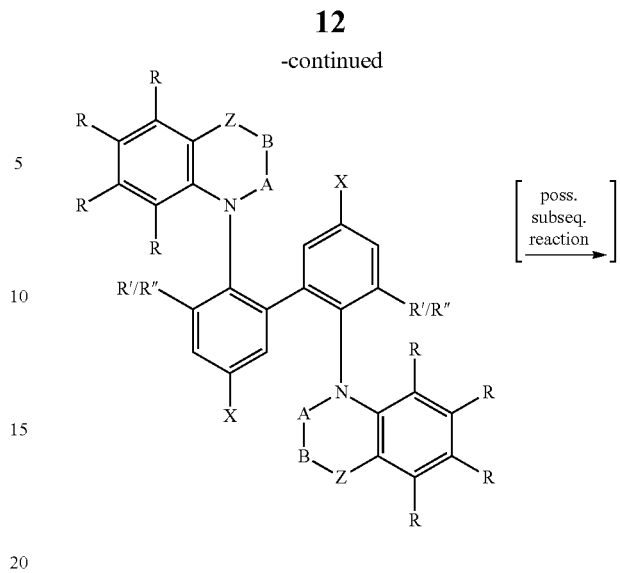

In this case a nitrogen heterocycle is reacted in a nucleophilic aromatic substitution with an aryl halide, in particular an aryl fluoride. Typical conditions include the use of a base, such as tribasic potassium phosphate or sodium hydride, for example, in an aprotic polar solvent, such as dimethyl sulfoxide (DMSO) or N,N-dimethylformamide (DMF), for example.

An alternative synthesis route comprises the introduction of a nitrogen heterocycle via copper- or palladium-catalyzed coupling to an aryl halide or aryl pseudohalide, in particular an aryl bromide, an aryl iodide, aryl triflate or an aryl tosylate.

The modes of preparation described may represent either the last synthetic reaction or else provide a precursor molecule which can be converted by subsequent reactions, as for example by altering the radicals R, R' and/or R", into the molecule of the invention.

A further aspect of the invention relates to the use of an organic molecule of the type described here as a luminescent emitter or as an absorber, and/or as host material and/or as electron transport material, and/or as hole injection material, and/or as hole blocking material in an organic optoelectronic device.

In the context of such use, the organic optoelectronic device is more particularly selected from the group consisting of:
  organic light-emitting diodes (OLEDs),
  light-emitting electrochemical cells,
  OLED sensors, especially in gas and vapour sensors not hermetically externally shielded,
  organic diodes,
  organic solar cells,
  organic transistors,
  organic field-effect transistors,
  organic lasers and
  down-conversion elements.

In the case of the use, the fraction of the organic molecule in the emission layer in an organic optoelectronic device, more particularly in OLEDs, is 1% to 99%, more particularly 5% to 80% (wt %). In an alternative embodiment the proportion of the organic molecule in the emission layer is 100%.

In one embodiment the light-emitting layer comprises not only the organic molecule of the invention but also a host material whose triplet (T1) and singlet (S1) energy levels are energetically higher than the triplet (T1) and singlet (S1) energy levels of the organic molecule.

In a further aspect, the invention relates to an organic optoelectronic device comprising an organic molecule of the type described here, more particularly in the form of a device selected from the group consisting of organic light-emitting diode (OLED), light-emitting electrochemical cell, OLED sensor, more particularly gas and vapour sensors not hermetically externally shielded, organic diode, organic solar cell, organic transistor, organic field-effect transistor, organic laser and down-conversion element.

An organic optoelectronic device of this kind has in one embodiment:
a substrate,
an anode and
a cathode, the anode or the cathode in particular being applied directly to the substrate, and
at least one light-emitting layer which is disposed between anode and cathode and which comprises the organic molecule of the invention.

In one embodiment the optoelectronic device is an OLED. A typical OLED has, for example, the following layer construction:
1. Substrate (support material)
2. Anode
3. Hole injection layer (HIL)
4. Hole transport layer (HTL)
5. Electron blocking layer (EBL)
6. Emitting layer (EML)
7. Hole blocking layer (HBL)
8. Electron transport layer (ETL)
9. Electron injection layer (EIL)
10. Cathode.

Certain layers are present only optionally. Moreover, a number of these layers may coincide with one another. And it is possible for certain layers to be present multiply in the component.

According to one embodiment, at least one electrode of the organic component is translucent in form. Here and below, "translucent" denotes a layer which is transmissive to visible light. This translucent layer may be transparently clear, i.e. transparent, or may be at least partly light-absorbing and/or partly light-scattering, so that the translucent layer may also, for example, have a diffuse or milky translucency. In particular, a layer identified here as translucent is as far as possible transparent in form, and so, in particular, the absorption of light is as small as possible.

According to a further embodiment, the organic component, more particularly an OLED, has an inverter construction. A feature of the inverter construction is that the cathode is located on the substrate and the other layers are applied, correspondingly, in inverted order:
1. Substrate (support material)
2. Cathode
3. Electron injection layer (EIL)
4. Electron transport layer (ETL)
5. Hole blocking layer (HBL)
6. Emitting layer (EML)
7. Electron blocking layer (EBL)
8. Hole transport layer (HTL)
9. Hole injection layer (HIL)
10. Anode Certain layers are present only optionally. Moreover, a number of these layers may coincide with one another. And it is possible for certain layers to be present multiply in the component.

In one embodiment, in the case of the inverted OLED, the anode layer of the typical construction, e.g. an ITO layer (indium tin oxide), is connected as cathode.

According to a further embodiment, the organic component, more particularly an OLED, has a stacked construction. In this case the individual OLEDs are arranged one above another and not, in the usual form, alongside one another. A stacked construction may permit the generation of mixed light. This construction may be used, for example, in the generation of white light, which is generated by imaging the entire visible spectrum typically through the combination of the emitted light from blue, green and red emitters. Furthermore, for virtually the same efficiency and identical luminance, significantly longer lifetimes can be achieved in comparison to conventional OLEDs. For the stacked construction, optionally, a layer known as a charge generation layer (CGL) is used between two OLEDs. This layer consists of an n-doped and a p-doped layer, the n-doped layer typically being applied closer to the anode.

In one embodiment—called a tandem OLED—there are two or more emission layers between anode and cathode. In one embodiment, three emission layers are arranged one above another, with one emission layer emitting red light, one emission layer emitting green light and one emission layer emitting blue light, and, optionally, further charge generation layers, blocking layers or transport layers are applied between the individual emission layers. In a further embodiment, the respective emission layers are applied directly adjacent. In another embodiment there is a charge generation layer between each of the emission layers. It is also possible for directly adjacent emission layers and emission layers separated by charge generation layers to be combined in an OLED.

Over the electrodes and the organic layers it is additionally possible for an encapsulating arrangement to be disposed. The encapsulating arrangement may be implemented for example in the form of a glass cover or in the form of a thin-film encapsulation.

Serving as support material for the optoelectronic device may be, for example, glass, quartz, plastic, metal, silicon wafer or any other suitable solid or flexible, optionally transparent material. The support material may comprise, for example, one or more materials in the form of a layer, a film, a plate or a laminate.

Serving as anode in the optoelectronic device may be, for example, transparent conducting metal oxides such as, for example, ITO (indium tin oxide), zinc oxide, tin oxide, cadmium oxide, titanium oxide, indium oxide or aluminium zinc oxide (AZO), $Zn_2SnO_4$, $CdSnO_3$, $ZnSnO_3$, $MgIn_2O_4$, $GaInO_3$, $Zn_2In_2O_5$ or $In_4Sn_3O_{12}$, or mixtures of different transparent conducting oxides.

Serving as materials of an HIL there may be, for example, PEDOT:PSS (poly-3,4-ethylenedioxythiophene:polystyrenesulfonic acid), PEDOT (poly-3,4-ethylenedioxythiophene), m-MTDATA (4,4',4''-tris[phenyl(m-tolyl)amino]triphenylamine), Spiro-TAD (2,2',7,7'-tetrakis(N,N-diphenylamino)-9,9-spirobifluorene), DNTPD (4,4'-bis[N-[4-{N,N-bis(3-methyl-phenyl)amino}phenyl]-N-phenylamino]biphenyl), NPNPB (N,N'-diphenyl-N,N'-di-[4-(N,N-diphenyl-amino)phenyl]benzene), MeO-TPD (N,N,N',N'-tetrakis(4-methoxyphenyl)benzene), HAT-CN (1,4,5,8,9,11-hexaazatriphenylenehexacarbonitrile) or Spiro-NPD (N,N'-diphenyl-N,N'-bis(1-naphthyl)-9,9'-spirobifluorene-2,7-diamine).

Serving as materials of an HTL may be tertiary amines, carbazole derivatives, polystyrenesulfonic acid-doped polyethylenedioxythiophene, camphorsulfonic acid-doped polyaniline, poly-TPD (poly(4-butylphenyldiphenylamine)), [alpha]-NPD (poly(4-butylphenyldiphenylamine)), TAPC (4,4'-cyclohexylidene-bis[N,N-bis(4-methylphenyl)- benzenamine]), TCTA (tris(4-carbazoyl-9-ylphenyl)amine), 2-TNATA (4,4',4''-tris[2-naphthyl(phenyl)amino]triphenylamine), Spiro-TAD, DNTPD, NPNPB, MeO-TPD, HAT-CN or TrisPcz (9,9'-diphenyl-6-(9-phenyl-9H-carbazol-3-yl)-9H,9'H-3,3'-bicarbazole).

The HTL may have a p-doped layer which comprises an inorganic or organic dopant in an organic hole-conducting matrix. Examples of inorganic dopants which an be utilized include transition metal oxides such as, for instance, vanadium oxide, molybdenum oxide or tungsten oxide. Organic dopants which can be used include, for example, tetrafluorotetracyanoquinodimethane (F4-TCNQ), copper pentafluorobenzoate (Cu(I)pFBz) or transition metal complexes.

Serving as materials of an electron blocking layer may be, for example, mCP (1,3-bis(carbazol-9-yl)benzene), TCTA, 2-TNATA, mCBP (3,3-di(9H-carbazol-9-yl)biphenyl), tris-Pcz (9,9'-diphenyl-6-(9-phenyl-9H-carbazol-3-yl)-9H,9'H-3,3'-bicarbazole), CzSi (9-(4-tert-butylphenyl)-3,6-bis(triphenylsilyl)-9H-carbazole), or DCB (N,N'-dicarbazolyl-1,4-dimethylbenzene).

The emitting layer EML comprises or consists of emitter material or a mixture comprising at least two emitter materials, and optionally of one or more host materials. Examples of suitable host materials are mCP, TCTA, 2-TNATA, mCBP, Sif87 (dibenzo[b,d]thiophen-2-yltriphenylsilane), Sif88 (dibenzo[b,d]thiophen-2-yl)diphenylsilane), CBP (4,4'-bis-(N-carbazolyl)biphenyl) or DPEPO (bis[2-((oxo)diphenylphosphino)phenyl] ether). For emitter material emitting in the green or in the red, or a mixture comprising at least two emitter materials, the common matrix materials such as CBP are suitable. For emitter material emitting in the blue or a mixture comprising at least two emitter materials, it is possible to use UHG matrix materials (Ultra-High energy Gap materials) (see, for example, M. E. Thompson et al., Chem. Mater. 2004, 16, 4743) or other so-called Wide-Gap matrix materials.

The hole blocking layer HBL may comprise, for example, BCP (2,9-dimethyl-4,7-diphenyl-1,10-phenanthroline=bathocuproin), bis(2-methyl-8-hydroxyquinolinato)-(4-phenylphenolato)-aluminium(III) (BAlq), Nbphen (2,9-bis(naphthalen-2-yl)-4,7-diphenyl-1,10-phenanthroline), Alq3 (aluminium-tris(8-hydroxyquinolin)), TSPO1 (diphenyl-4-triphenylsilylphenylphosphine oxide) or TCB/TCP (1,3,5-tris(N-carbazolyl)benzene/1,3,5-tris(carbazol-9-yl)benzene).

The electron transport layer ETL may comprise, for example, materials based on AlQ$_3$, TSPO1, BPyTP2 (2,7-di(2,2'-bipyridin-5-yl)triphenyl) or BTB (4,4'-bis[2-(4,6-diphenyl-1,3,5-triazinyl)]-1,1'-biphenyl).

Examples of materials which can be used in a thin electron injection layer EIL include CsF, LiF, 8-hydroxyquinolinolatolithium (Liq), Li$_2$O, BaF$_2$, MgO or NaF.

Serving as materials of the cathode layer may be metals or alloys, for example Al, Al>AlF, Ag, Pt, Au, Mg, Ag:Mg. Typical layer thicknesses are 100 nm to 200 nm. In particular, use is made of one or more metals which are stable in air and/or which are self-passivating, by formation of a thin protective oxide layer, for example.

Examples of materials suitable for encapsulation are aluminium oxide, vanadium oxide, zinc oxide, zirconium oxide, titanium oxide, hafnium oxide, lanthanum oxide and tantalum oxide. The skilled person here is aware of which combinations of the materials to use for an optoelectronic device comprising an organic molecule of the invention.

In one embodiment of the organic optoelectronic device of the invention, the organic molecule of the invention is used as emission material in a light-emitting layer, being used either as a pure layer or in combination with a matrix material.

The fraction of the organic molecule of the invention in the emission layer in a further embodiment, in a light-emitting layer in optical light-emitting devices, more particularly in OLEDs, is between 5% and 80%. In one embodiment of the organic optoelectronic device of the invention, the light-emitting layer is applied to a substrate; in particular an anode and a cathode are applied to the substrate and the light-emitting layer is applied between anode and cathode.

The light-emitting layer may exclusively have an organic molecule of the invention at 100% concentration, with the anode and the cathode applied to the substrate, and the light-emitting layer applied between anode and cathode.

In one embodiment of the organic optoelectronic device of the invention, a hole and electron injecting layer is applied between anode and cathode, and a hole and electron transporting layer is applied between hole and electron injecting layer, and the light-emitting layer is applied between hole and electron transporting layer.

In a further embodiment of the invention, the organic optoelectronic device comprises the following: a substrate, an anode, a cathode, and in each case at least one hole and electron injecting layer, and in each case at least one hole and electron transporting layer, and at least one light-emitting layer, comprising organic molecule of the invention and a host material whose triplet (T1) and singlet (S1) energy levels are energetically higher than the triplet (T1) and singlet (S1) energy levels of the organic molecule, with the anode and the cathode being applied to the substrate, and the hole and electron injecting layer being applied between anode and cathode, and the hole and electron transporting layer being applied between hole and electron injecting layer, and the light-emitting layer being applied between hole and electron transporting layer.

Also in accordance with the invention is a light-emitting material comprising an organic molecule of the invention and a host material, the triplet (T1) and singlet (S1) energy levels of the host material being energetically higher than the triplet (T1) and singlet (S1) energy levels of the organic molecule, where the light-emitting material emits fluorescence or thermally activated delayed fluorescence, and has a deltaE(S1−T1) value between the lowermost excited singlet (S1) state and the triplet (T1) state beneath it of less than 3000 cm$^{-1}$.

In a further aspect, the invention relates to a method for producing an optoelectronic component. In this case an organic molecule of the invention is used.

In one embodiment, the production method comprises the processing of the organic molecule of the invention by means of a vacuum evaporation process or from a solution.

Also in accordance with the invention is a method for producing an optoelectronic device of the invention that comprises at least one layer of the optoelectronic device being coated by a sublimation process, being coated by an OVPD (Organic Vapour Phase Deposition) process, being coated by carrier gas sublimation, and/or being produced from solution or by a printing process.

EXAMPLES

General Operating Protocols: Photophysical Measurements

Pretreatment of Optical Glasses

After each use, the optical glasses (cuvettes and substrates made of fused silica, diameter: 1 cm) are cleaned. Washed three times each with dichloromethane, acetone, ethanol, demineralized water. Placed in 5% Hellmanex solution for 24 h, rinsed off thoroughly with demineralized water, blown with nitrogen to dry the optical glasses.

Sample Preparation: Solutions 1-2 mg of the sample were dissolved in 100 ml of the respective solvent, concentration $10^{-5}$ mol/l. The cuvette was given an airtight closure and degassed for 10 minutes.

Sample Preparation, Film: Spin Coating

Instrument: Spin150, SPS euro.

The sample concentration was 10 mg/ml, prepared in toluene or chlorobenzene.

Program: 1) 3 s at 400 rpm; 2) 20 s at 1000 rpm at 1000 rpm/s (rotations per minute/second); 3) 10 s at 4000 rpm at 1000 rpm/s. After coating, the films were dried in air at 70° C. for 1 minute on a precision hotplate from LHG.

Absorption Spectroscopy

Solutions:

UV-VIS spectra were recorded on an Evolution 201 instrument from Thermo Scientific. (See sample preparation: solutions)

Photoluminescence Spectroscopy and TCSPC

Steady-state emission spectroscopy is carried out using a FluoroMax-4 fluorescence spectrometer from Horiba Scientific, equipped with a 150 W xenon arc lamp, excitation and emission monochromators and a Hamamatsu R928 photomultiplier tube, and also with a TCSPC option. Emission and excitation spectra were corrected using standard correction plots.

Determination of Quantum Efficiency

The photoluminescent quantum yield was measured using an Absolute PL Quantum Yield Measurement C9920-03G system from Hamamatsu Photonics. This system consists of a 150 W xenon gas discharge lamp, automatically adjustable Czerny-Turner monochromators (250-950 nm) and an Ulbricht sphere with highly reflective Spektralon (a Teflon derivative) coating, connected via a glass fibre cable to a PMA-12 multichannel detector with BT (back thinned) CCD chip with 1024×122 pixels (size 24×24 µm). The quantum efficiency and the CIE coordinates were analyzed using the U6039-05 software, version 3.6.0.

The emission maximum is reported in nm, the quantum yield $\phi$ in % and the CIE colour coordinates as x,y values.

PLQY was determined for polymer films, solutions and powder samples in accordance with the following protocol:

The reference material used is anthracene in ethanol at known concentration. First the absorption maximum of the sample was determined, and used to excite the sample. Subsequently the absolute quantum yield was determined on degassed solutions and films under a nitrogen atmosphere.

The calculation was made by the system itself in accordance with the following equation:

$$\Phi_{PL} = \frac{n_{photon, emitted}}{n_{photon, absorbed}} = \frac{\int \frac{\lambda}{hc}\left[Int_{emitted}^{Sample}(\lambda) - Int_{absorbed}^{Sample}(\lambda)\right]d\lambda}{\int \frac{\lambda}{hc}\left[Int_{emitted}^{Reference}(\lambda) - Int_{absorbed}^{Reference}(\lambda)\right]d\lambda}$$

with the photon number $n_{photon}$ and the intensity Int.

Calculations According to Density Functional Theory

Molecular structures were optimized using the BP86 functional (Becke, A. D. Phys. Rev. A1988, 38, 3098-3100; Perdew, J. P. Phys. Rev. B1986, 33, 8822-8827), employing the resolution-of-identity (RI) approximation (Sierka, M.; Hogekamp, A.; Ahlrichs, R. J. Chem. Phys. 2003, 118, 9136-9148; Becke, A. D., J. Chem. Phys. 98 (1993) 5648-5652; Lee, C; Yang, W; Parr, R. G. Phys. Rev. B 37 (1988) 785-789). Excitation energies were calculated in the case of the structure optimized with BP86 by the time-dependent DFT (TD-DFT) method using the B3LYP functional (Becke, A. D., J. Chem. Phys. 98 (1993) 5648-5652; Lee, C; Yang, W; Parr, R. G. Phys. Rev. B 37 (1988) 785-789; Vosko, S. H.; Wilk, L.; Nusair, M. Can. J. Phys. 58 (1980) 1200-1211; Stephens, P. J.; Devlin, F. J.; Chabalowski, C. F.; Frisch, M. J. J. Phys. Chem. 98 (1994) 11623-11627). All calculations use def2-SV(P) base sets (Weigend, F.; Ahlrichs, R. Phys. Chem. Chem. Phys. 2005, 7, 3297-3305; Rappoport, D.; Furche, F. J. Chem. Phys. 2010, 133, 134105/1-134105/11) and an m4 grid for numeric integration. All DFT calculations were carried out using the Turbomole program package (Version 6.5) (TURBOMOLE V6.4 2012, a development of University of Karlsruhe and Forschungszentrum Karlsruhe GmbH, 1989-2007, TURBOMOLE GmbH, since 2007; available from http://www.turbomole.com).

Example 1

Synthesis (Stage 1):

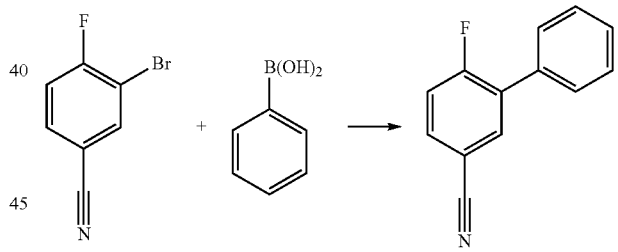

3-Bromo-4-fluorobenzonitrile (125 mmol), phenylboronic acid (188 mmol), palladium acetate (2.5 mmol), 2-dicyclohexylphosphino-2',6'-dimethoxy-1,1'-biphenyl (SPhos; 5 mmol) and tribasic potassium phosphate (250 mmol) are suspended under nitrogen in 200 ml of toluene. Following addition of 10 ml of degassed water, the reaction mixture is blanketed with nitrogen for 20 min. After stirring at 110° C. for 18 h and cooling to room temperature, the reaction solution is filtered and the solid is washed with ethyl acetate. The filtrate is dried over MgSO$_4$. Following removal of the solvent, the crude product is recrystallized from n-hexane. 3-Phenyl-4-fluorobenzonitrile (15.9 g, 80.6 mmol, 64%) is obtained as a white solid.

$^1$H NMR (500 MHz, chloroform-d) δ 7.77 (dd, J=7.1, 2.2 Hz, 1H) 7.64 (ddd, J=8.5, 4.5, 2.2 Hz, 1H), 7.54-7.42 (m, 5H) 7.27 (dd, J=9.9, 8.5 Hz, 1H).

Stage 2:

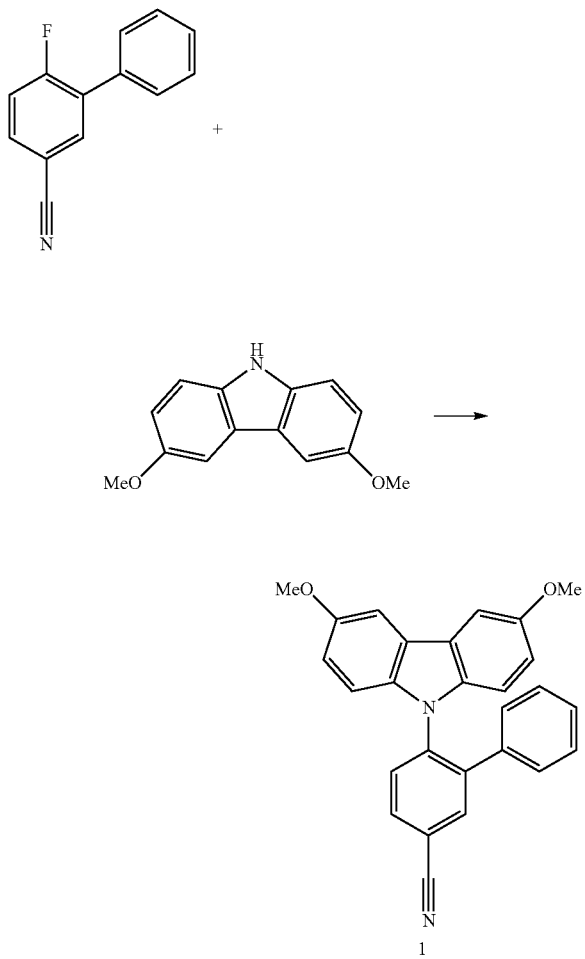

Example 2

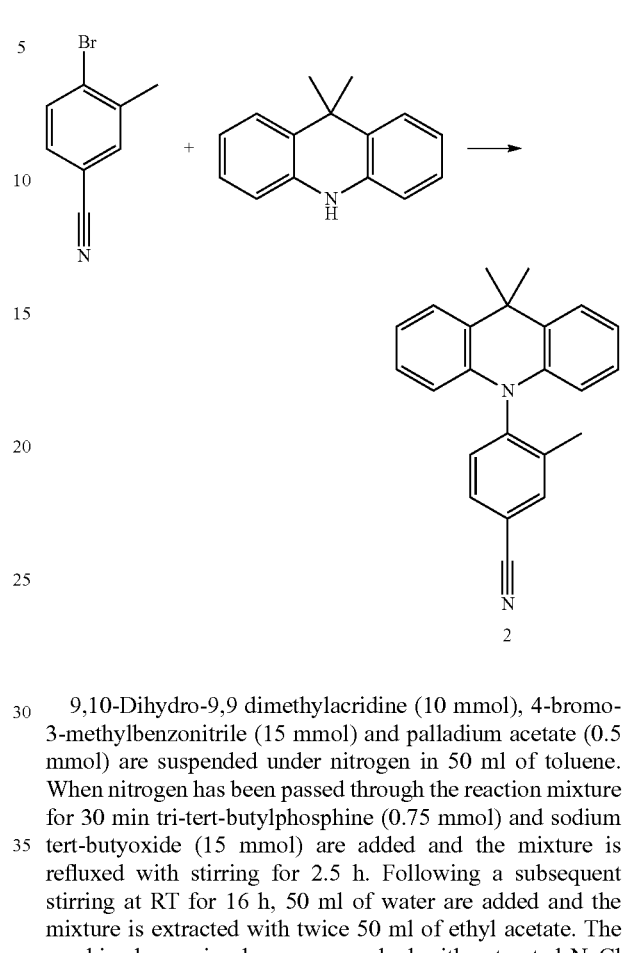

3-Phenyl-4-fluorobenzonitrile (65.9 mmol), 3,6-dimethoxycarbazole (65.9 mmol) and tribasic potassium phosphate (132 mmol) are suspended under nitrogen in DMSO (120 ml) and stirred at 110° C. (16 h). The reaction mixture is subsequently introduced into 700 ml of water and stirred for 1 h. The solid is isolated by filtration and washed with water (1 l). The solid is subsequently dried under reduced pressure at 50° C. The crude product is purified by recrystallization from toluene. The product 1 (23.1 g, 57.1 mmol, 87%) is obtained as a white solid.

$^1$H NMR (500 MHz, chloroform-d) δ 7.95 (d, J=1.9 Hz, 1H), 7.80 (dd, J=8.2, 2.0 Hz, 1H), 7.64 (d, J=8.1 Hz, 1H), 7.45 (d, J=2.4 Hz, 2H), 7.10-7.02 (m, 3H), 7.02-6.98 (m, 2H), 6.92 (dd, J=8.9, 0.7 Hz, 2H), 6.89 (dd, J=8.9, 2.3 Hz, 2H) 3.90 (s, 6H).

Figure 2:
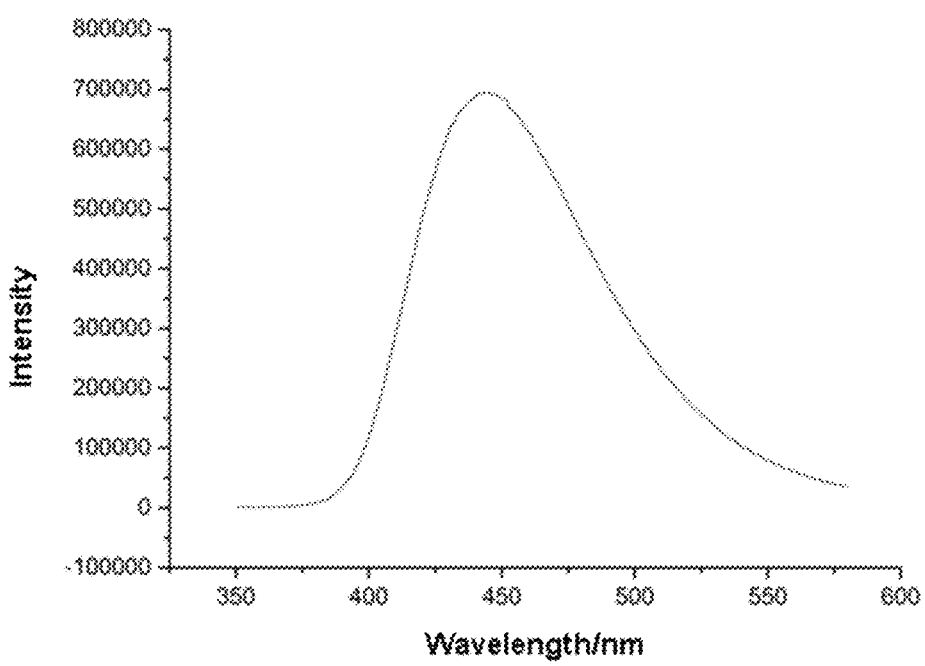
FIG. 2 is a film emission of 1 (10% in PMMA).

The absorption spectrum of 1 as a solution in 2-methyl-tetrahydrofuran is shown in FIG. 1. The film emission of 1 (10% in PMMA) can be seen in FIG. 2. The emission maximum is at 443 nm. The photoluminescence quantum yield (PLQY) is 56%.

The density functional theory calculations give a singlet (S1) energy of 2.86 eV and a triplet (T1) energy of 2.59 eV.

Figure 3:
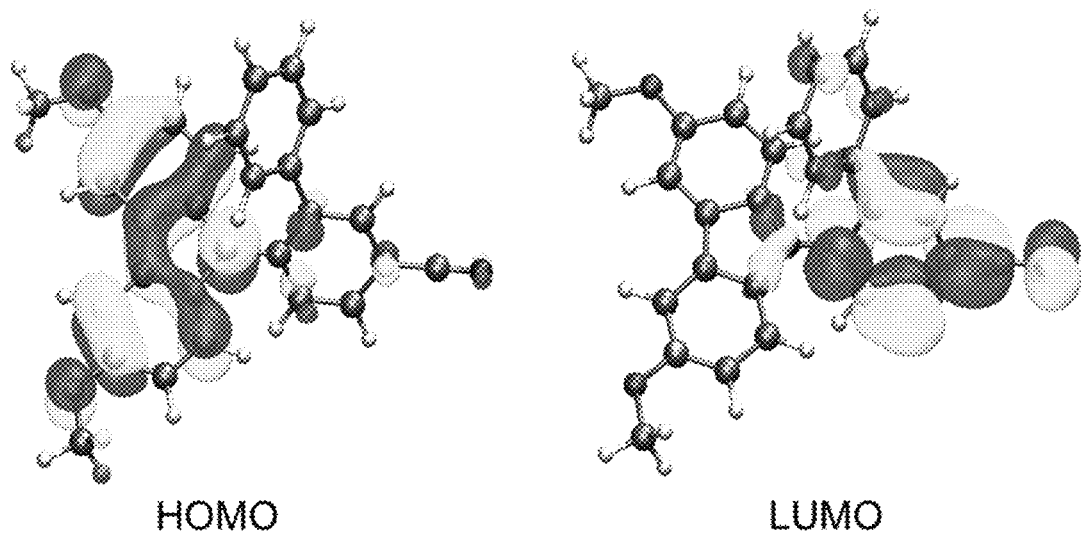
FIG. 3 illustrates the calculated frontier orbitals of the ground state of 1.

The calculated frontier orbitals of the ground state of 1 are shown in FIG. 3.

9,10-Dihydro-9,9 dimethylacridine (10 mmol), 4-bromo-3-methylbenzonitrile (15 mmol) and palladium acetate (0.5 mmol) are suspended under nitrogen in 50 ml of toluene. When nitrogen has been passed through the reaction mixture for 30 min tri-tert-butylphosphine (0.75 mmol) and sodium tert-butyoxide (15 mmol) are added and the mixture is refluxed with stirring for 2.5 h. Following a subsequent stirring at RT for 16 h, 50 ml of water are added and the mixture is extracted with twice 50 ml of ethyl acetate. The combined organic phases are washed with saturated NaCl solution and dried over MgSO$_4$. Following removal of the solvent, the residue is recrystallized from ethanol. 1.6 g (4.9 mmol, 49%) of the product 2 are obtained.

$^1$H NMR (500 MHz, chloroform-d) δ 7.81 (d, J=1.9 Hz, 1H), 7.75 (dd, J=8.1, 1.9 Hz, 1H), 7.53-7.46 (m, 2H) 7.38 (d, J=8.0 Hz, 1H), 7.04-6.91 (m, 4H), 6.07-5.97 (m, 2H), 2.14 (s, 3H), 1.74 (s, 3H) 1.68 (s, 3H).

Figure 4:
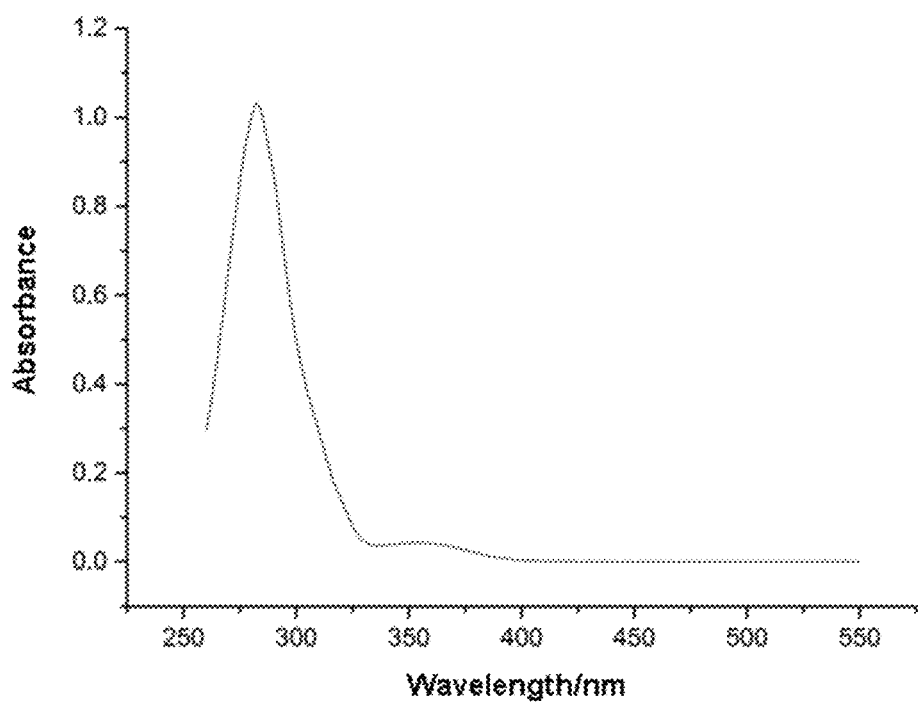
FIG. 4 is an absorption spectrum of 2 as a solution in 2-methyltetrahydrofuran.
Figure 5:
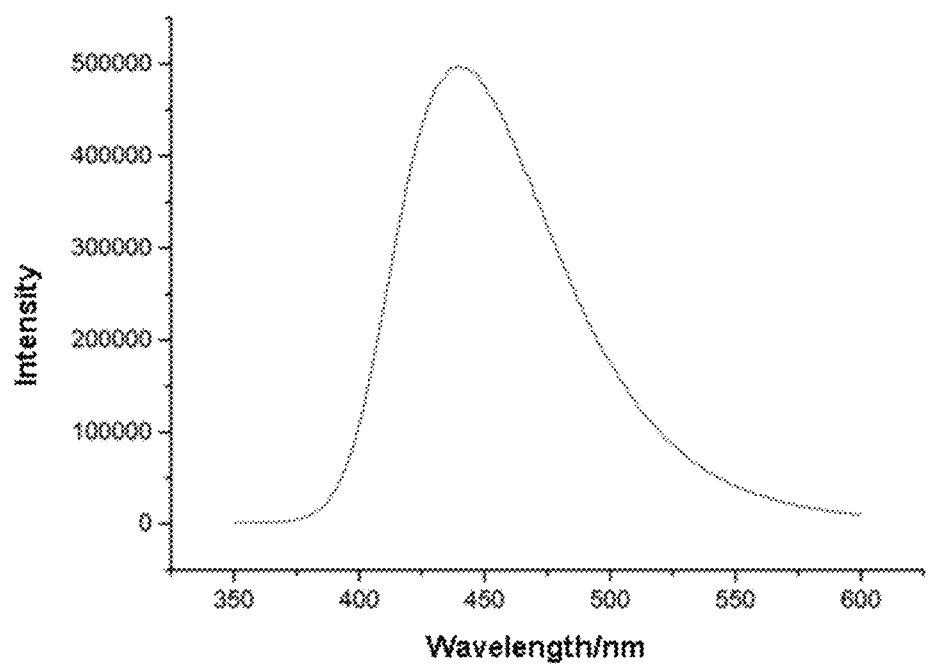
FIG. 5 is a film emission of 2 (10% in PMMA).

The absorption spectrum of 2 as a solution in 2-methyl-tetrahydrofuran is shown in FIG. 4. Film emission of 2 (10% in PMMA) can be seen in FIG. 5. The emission maximum is at 441 nm. The photoluminescence quantum yield (PLQY) is 55%.

Example 3

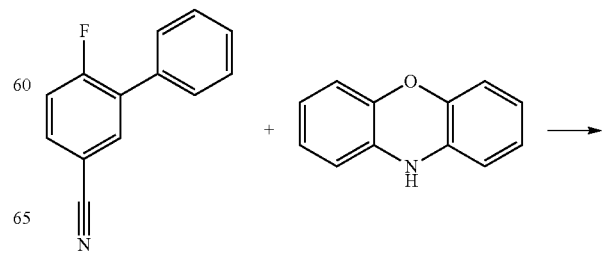

-continued

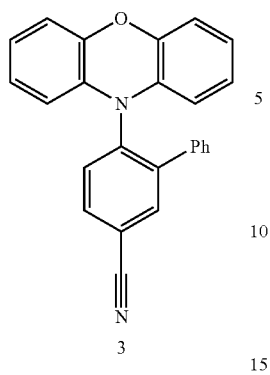

3

3-Phenyl-4-fluorobezonitrile (10 mmol), 2,3:5,6-dibenzo-1,4-oxazine (10 mmol) and tribasic potassium phosphate (20 mmol) are suspended under nitrogen in DMSO (20 ml) and stirred at 125° C. (14 h). The reaction mixture is then introduced into 400 ml of sat. sodium chloride solution and extracted with dichloromethane (3×150 ml). The combined organic phases are washed with saturated sodium chloride solution (2×150 ml) and dried over magnesium sulfate and then the solvent is removed. The crude product, finally, was purified by recrystallization from toluene. The product 3 was obtained as a yellow solid.

$^1$H NMR (500 MHz, chloroform-d) δ 7.91 (d, J=1.9 Hz, 1H), 7.85 (dd, J=8.1, 2.0 Hz, 1H), 7.57 (d, J=8.1 Hz, 1H), 7.35-7.29 (m, 5H), 6.65-6.59 (m, 4H), 6.59-6.54 (m, 2H), 5.90-5.83 (m, 2H).

Figure 6:
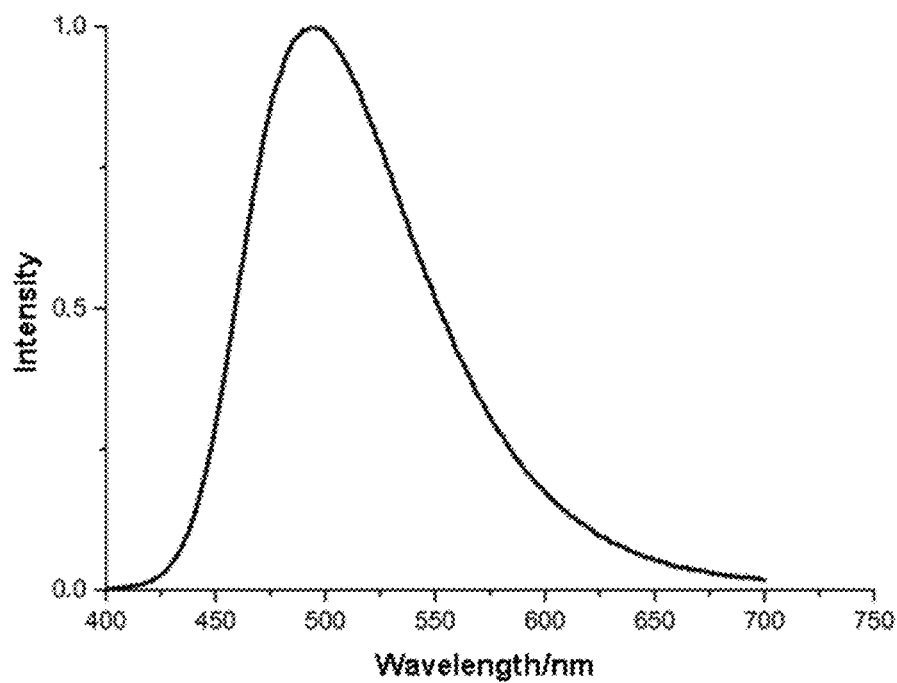
FIG. 6 is a film emission of 3 (10% in PMMA).

The film emission of 3 (10% in PMMA) can be seen in FIG. 6. The emission maximum is at 494 nm. The photoluminescence quantum yield (PLQY) is 65%.

Example 4

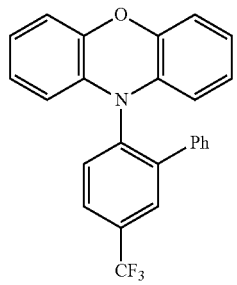

4

$^1$H NMR (500 MHz, Chloroform-d) δ 7.88 (s, 1H), 7.83 (d, J=7.6 Hz, 1H), 7.57 (d, J=8.2 Hz, 1H), 7.39-7.27 (m, 5H), 6.69-6.51 (m, 6H), 5.89 (d, J=7.6 Hz, 2H).

Figure 7:
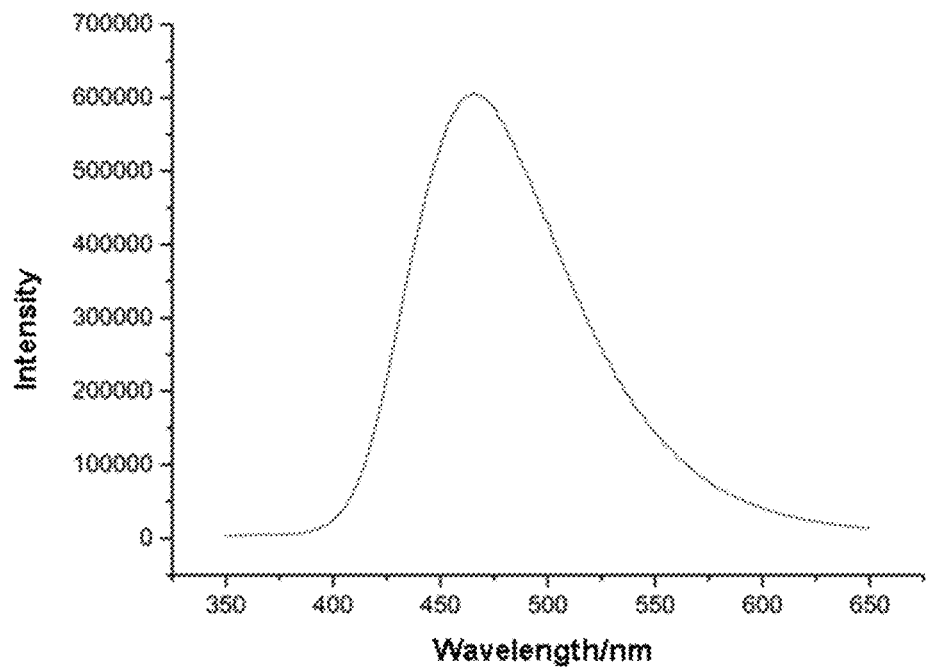
FIG. 7 is a film emission of 4 (10% in PMMA).

The film emission of 4 (10% in PMMA) can be seen in FIG. 7. The emission maximum is at 466 nm. The photoluminescence quantum yield (PLQY) is 31%. The emission lifetime is 51 μs.

Example 5

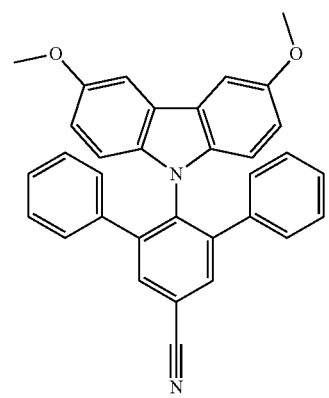

5

$^1$H NMR (500 MHz, chloroform-d) δ 7.87 (s, 2H), 7.30 (d, J=2.4 Hz, 2H) 7.05-7.00 (m, 2H), 6.99-6.94) (m, 4H), 6.94-6.89 (m, 4H), 6.77 (dd, J=8.8, 2.4 Hz, 2H), 6.72 (d, J=8.8 Hz, 2H), 3.84 (s, 6H).

Figure 8:
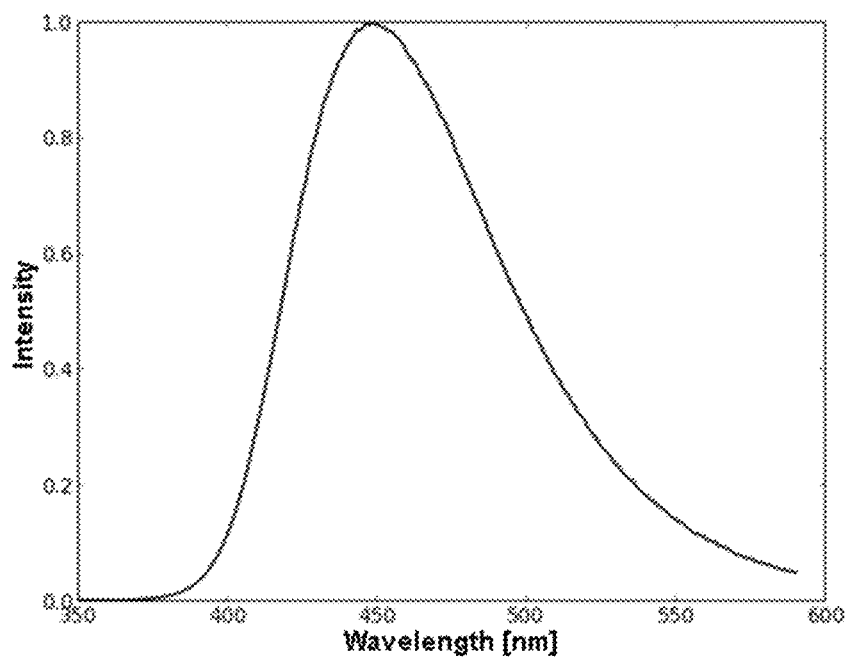
FIG. 8 is a film emission of 5 (10% in PMMA).

The film emission of 5 (10% in PMMA) can be seen in FIG. 8. The emission maximum is at 449 nm. The photoluminescence quantum yield (PLQY) is 65%.

Example 6

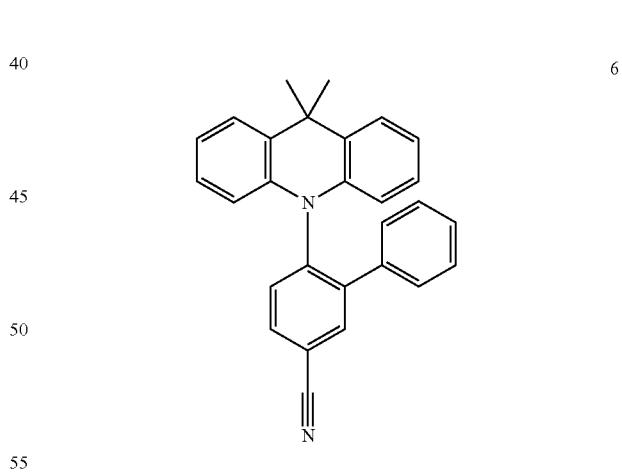

6

$^1$H NMR (500 MHz, chloroform-d) δ=7.93 (d, 1H), 7.90 (dd, 1H), 7.48 (d, 1H), 7.38 (dd, 2H), 7.21-7.13 (m, 5H), 6.97 (dt, 2H) 6.91 (dt, 2H), 6.15 (dd, 2H), 1.80 (s, 3H), 1.04 (s, 3H) ppm.

Figure 9:
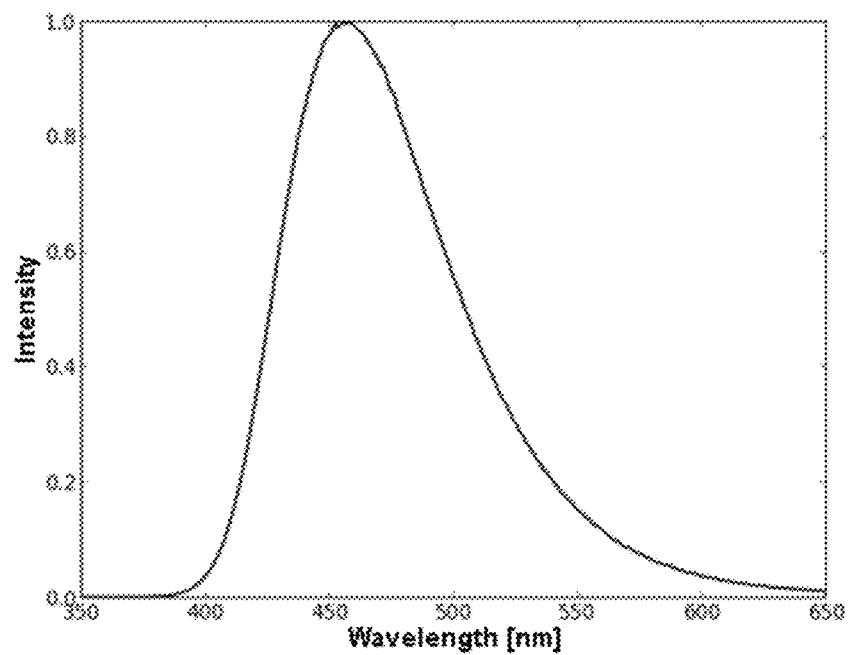
FIG. 9 is a film emission of 6 (10% in PMMA).

The film emission of 6 (10% in PMMA) can be seen in FIG. 9. The emission maximum is at 456 nm. The photoluminescence quantum yield (PLQY) is 60%.

Example 7

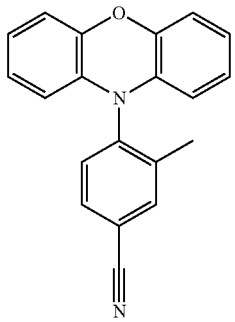

7

¹H NMR (500 MHz, chloroform-d) δ 7.77 (d, J=1.8 Hz, 1H), 7.72 (dd, J=8.0, 1.9 Hz, 1H), 7.43 (d, J=8.0 Hz, 1H), 6.76-6.65 (m, 4H), 6.60 (td, J=7.6, 1.7 Hz, 2H), 5.71 (dd, J=7.9, 1.4 Hz, 2H), 2.29 (s, 3H).

Figure 10:
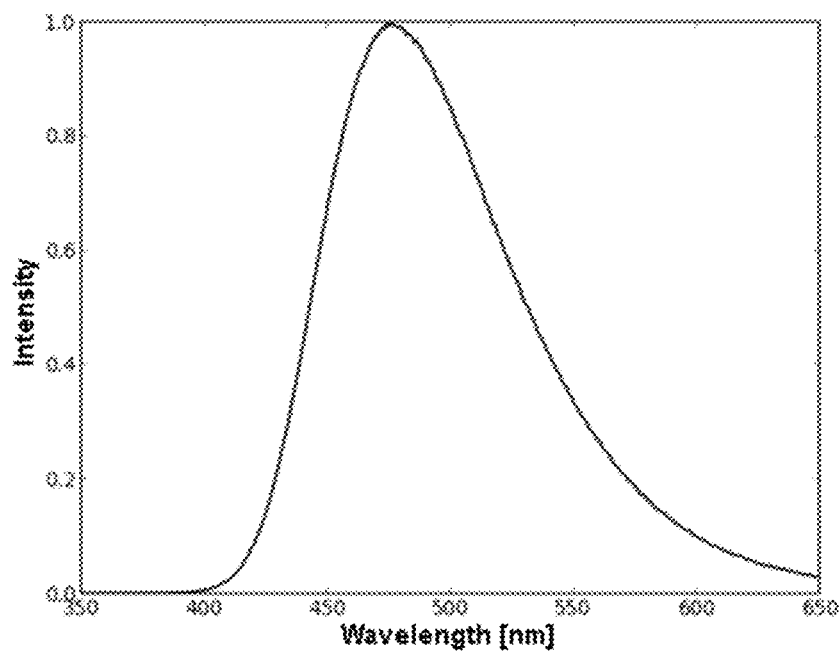
FIG. 10 is a film emission of 7 (10% in PMMA).

The film emission of 7 (10% in PMMA) can be seen in FIG. 10. The emission maximum is at 477 nm. The photoluminescence quantum yield (PLQY) is 71%.

Example 8

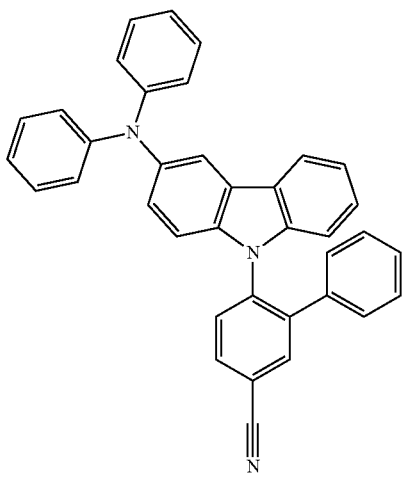

8

¹H NMR (500 MHz, chloroform-d) δ=7.98 (d, 1H), 7.89 (d, 1H), 7.85 (dd, 1H), 7.77 (d, 1H), 7.72 (d, 1H), 7.31-7.27 (m, 1H), 7.23-7.16 (m, 5H), 7.14-7.11 (m, 1H), 7.08-7.01 (8H), 6.98-6.94 (m, 4H), 6.88 (d, 1H) ppm.

Figure 11:
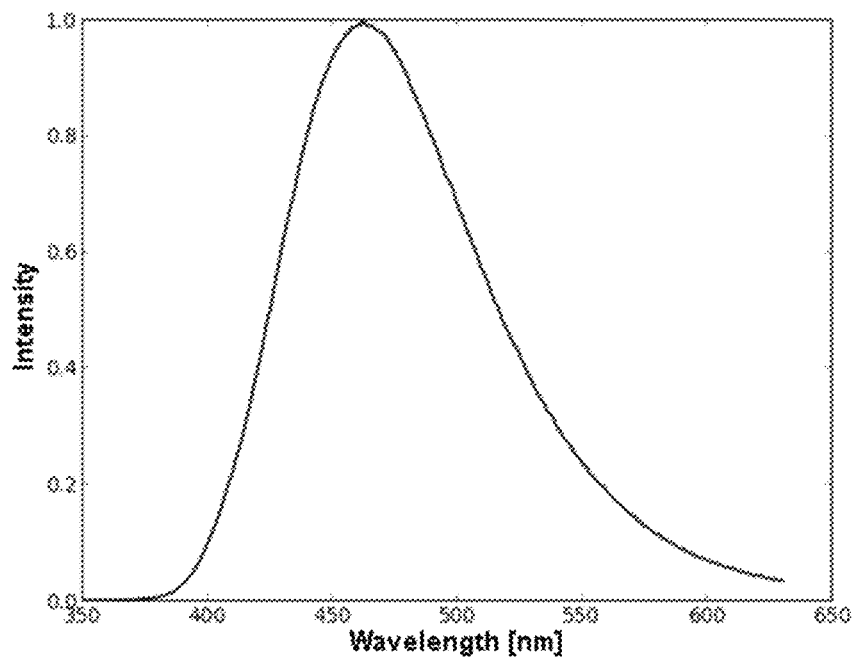
FIG. 11 is a film emission of 8 (10% in PMMA).

The film emission of 8 (10% in PMMA) can be seen in FIG. 11. The emission maximum is at 462 nm. The photoluminescence quantum yield (PLQY) is 40%.

Example 9

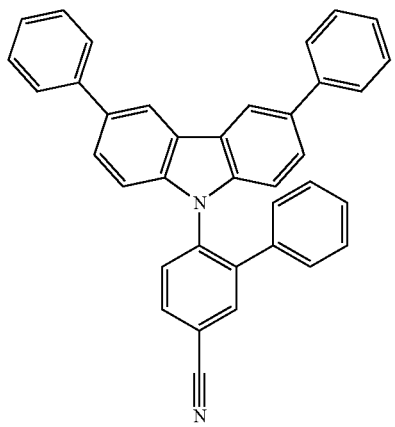

9

¹H NMR (500 MHz, chloroform-d) δ=8.30 (d, 2H), 8.02 (d, 1H), 7.87 (d, 1H), 7.72 (d, 1H), 7.68 (dd, 4H), 7.55 (dd, 2H), 7.47 (t, 4H), 7.35 (t, 2H), 7.11-7.04 (m, 7H) ppm.

Figure 12:
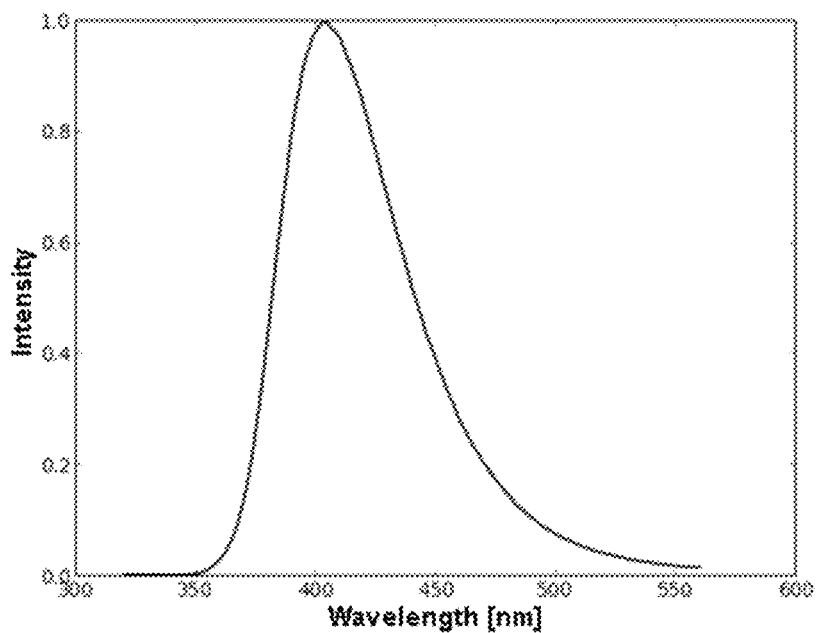
FIG. 12 is a film emission of 9 (10% in PMMA).

The film emission of 9 (10% in PMMA) can be seen in FIG. 12. The emission maximum is at 404 nm. The photoluminescence quantum yield (PLQY) is 28%.

Example 10—OLED Component A

Molecule 1 was tested in an OLED component having the following construction: ITO/m-MTDATA/HAT-CN/tris-Pcz/1:DPEPO (20%)/TSPO1/BPyTP2/Liq/Al.

TABLE 1

| Component data for component A. | |
|---|---|
| Power efficiency | 7.5 lm/W |
| Current efficiency | 9.7 cd/A |
| CIE | CIEx: 0.16 |
| | CIEy: 0.176 |
| | @ 13 V |
| External quantum yield (EQE) | 6.8% |

Figure 13:
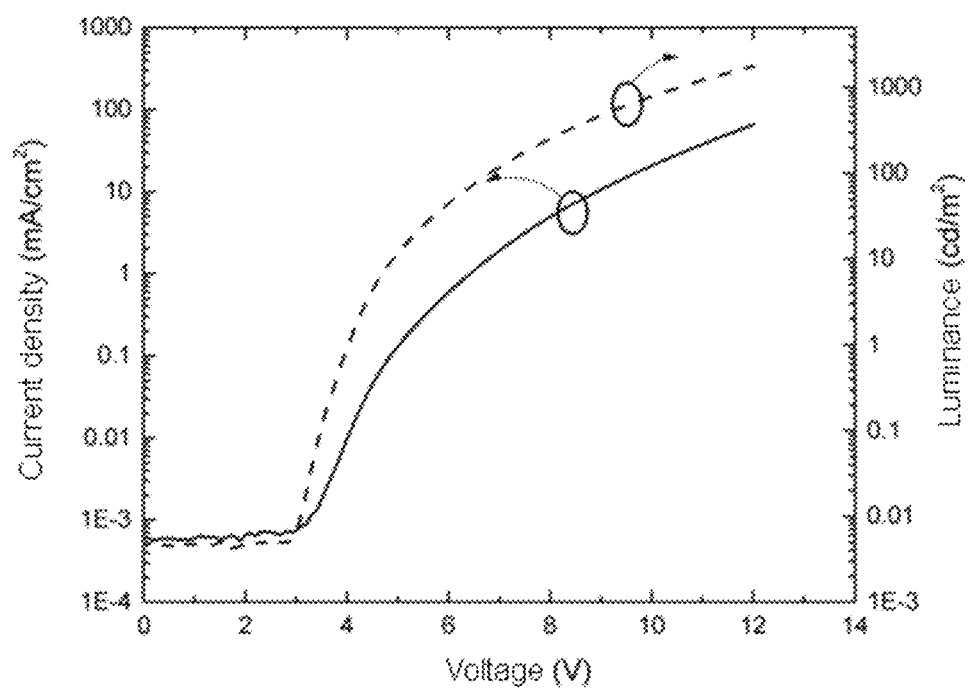
FIG. 13 is a current density and luminance of OLED component ITO/m-MTDATA/HAT-CN/tris-Pcz/1:DPEPO (20%)/TSPO1/BPyTP2/Liq/Al.
Figure 14:
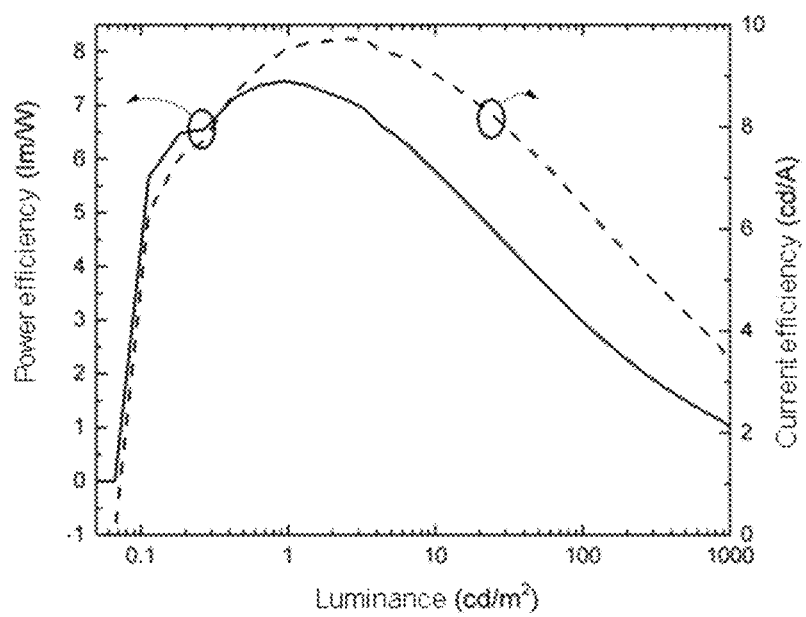
FIG. 14 is a power efficiency and current efficiency against the voltage of OLED component ITO/m-MTDATA/HAT-CN/tris-Pcz/1:DPEPO (20%)/TSPO1/BPyTP2/Liq/Al.
Figure 15:
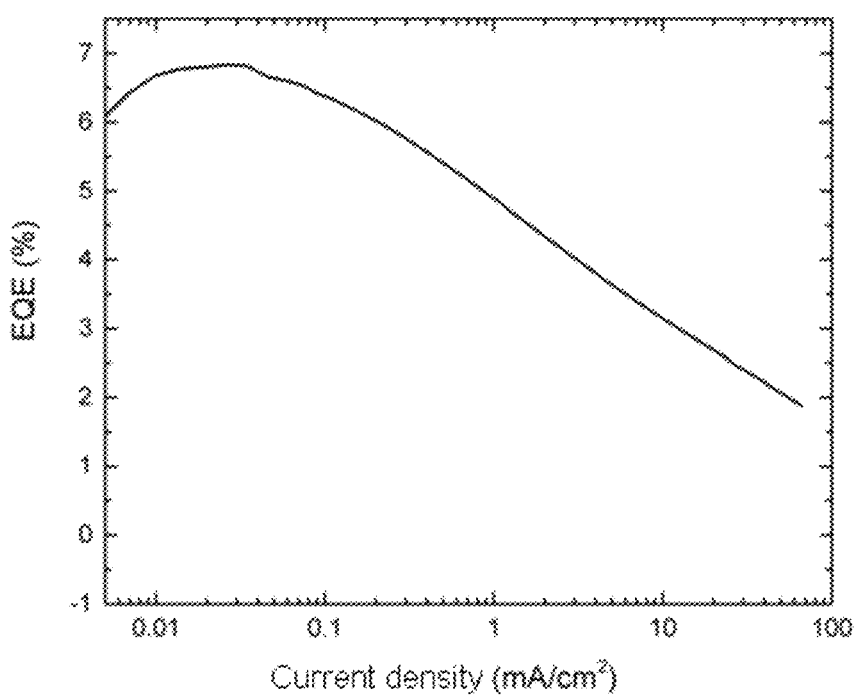
FIG. 15 is an external quantum efficiency against the current density of OLED component ITO/m-MTDATA/HAT-CN/tris-Pcz/1:DPEPO (20%)/TSPO1/BPyTP2/Liq/Al.
Figure 16:
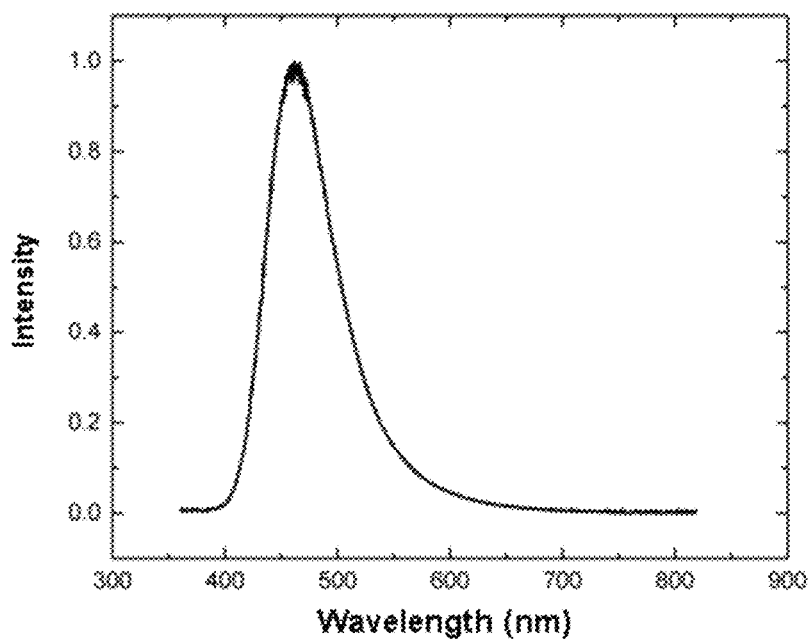
FIG. 16 is an electroluminescence spectrum on operation at 10 V of the OLED component ITO/m-MTDATA/HAT-CN/tris-Pcz/1:DPEPO (20%)/TSPO1/BPyTP2/Liq/Al.
Figure 17:
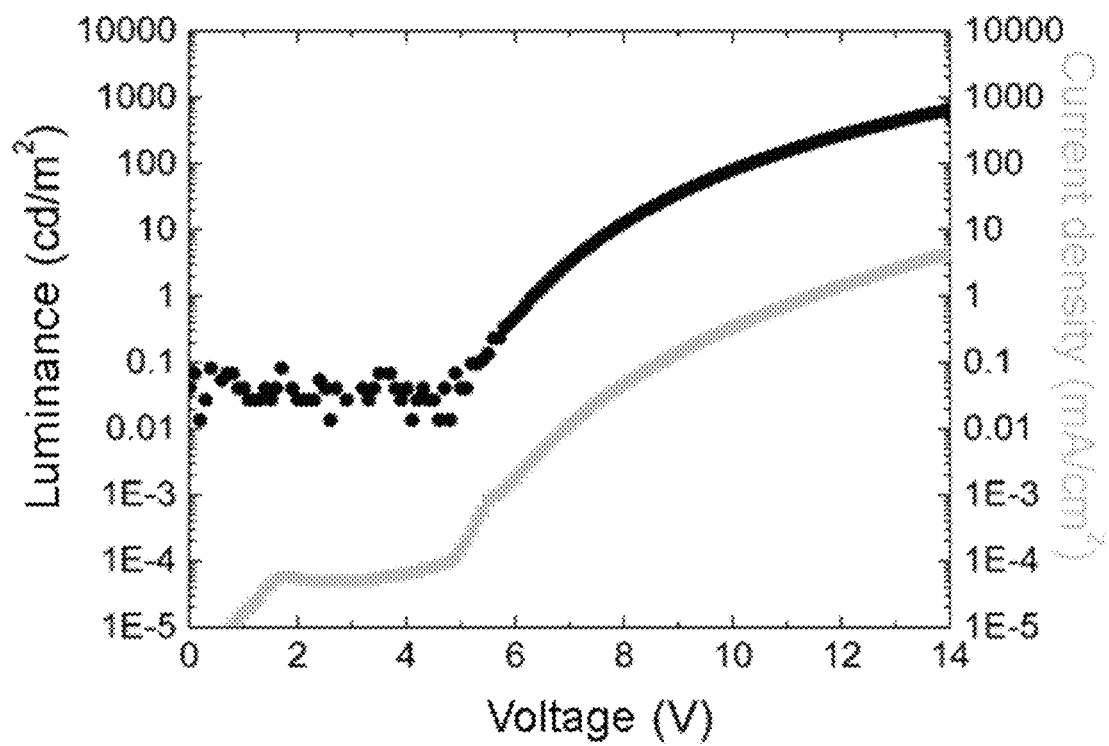
FIG. 17 is a current density and luminance of OLED component X2.
Figure 18:
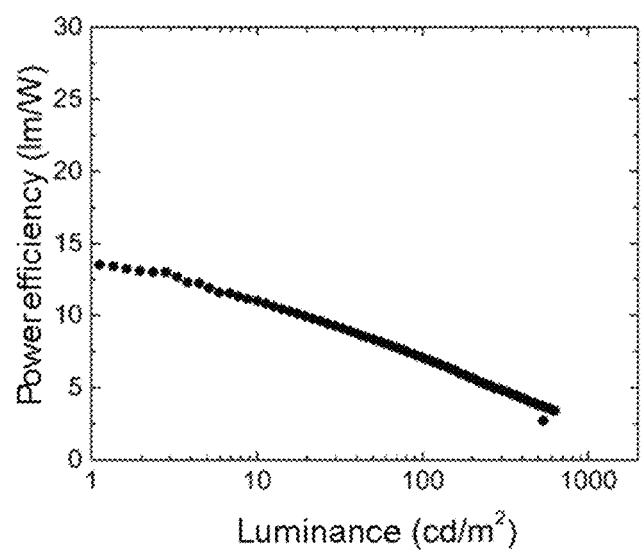
FIG. 18 is a power efficiency of OLED component X2
Figure 19:
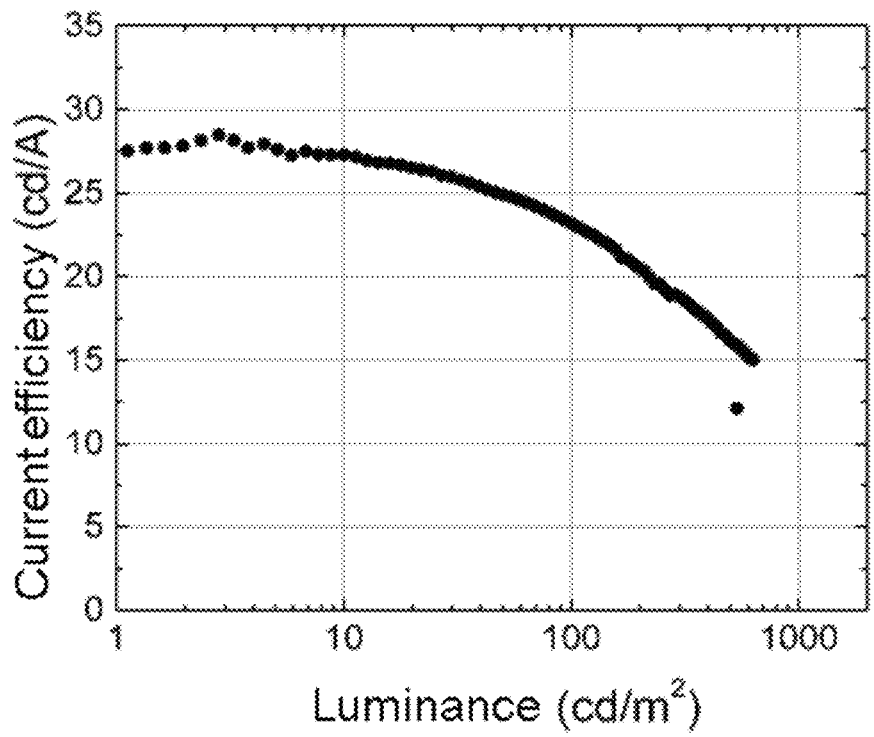
FIG. 19 is a current efficiency of OLED component X2.
Figure 20:
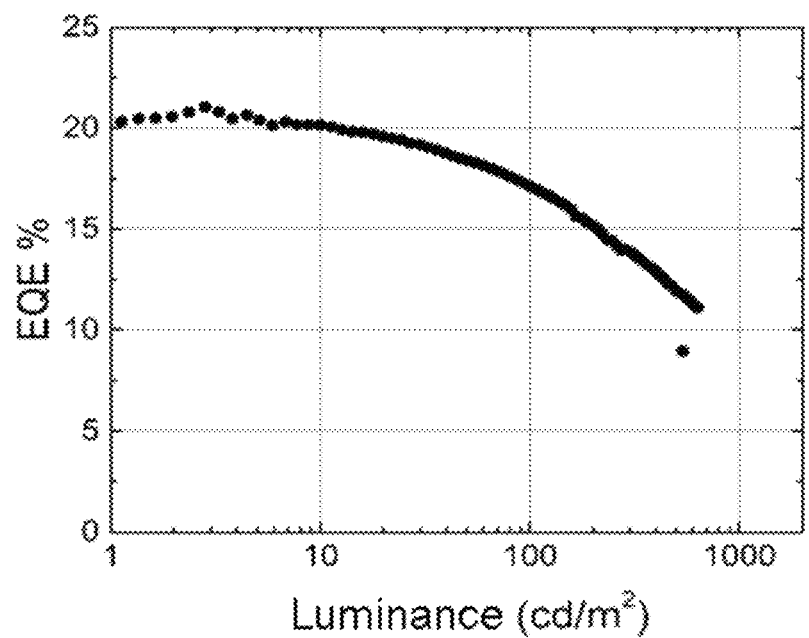
FIG. 20 is an external quantum efficiency of OLED component X2.
Figure 21:
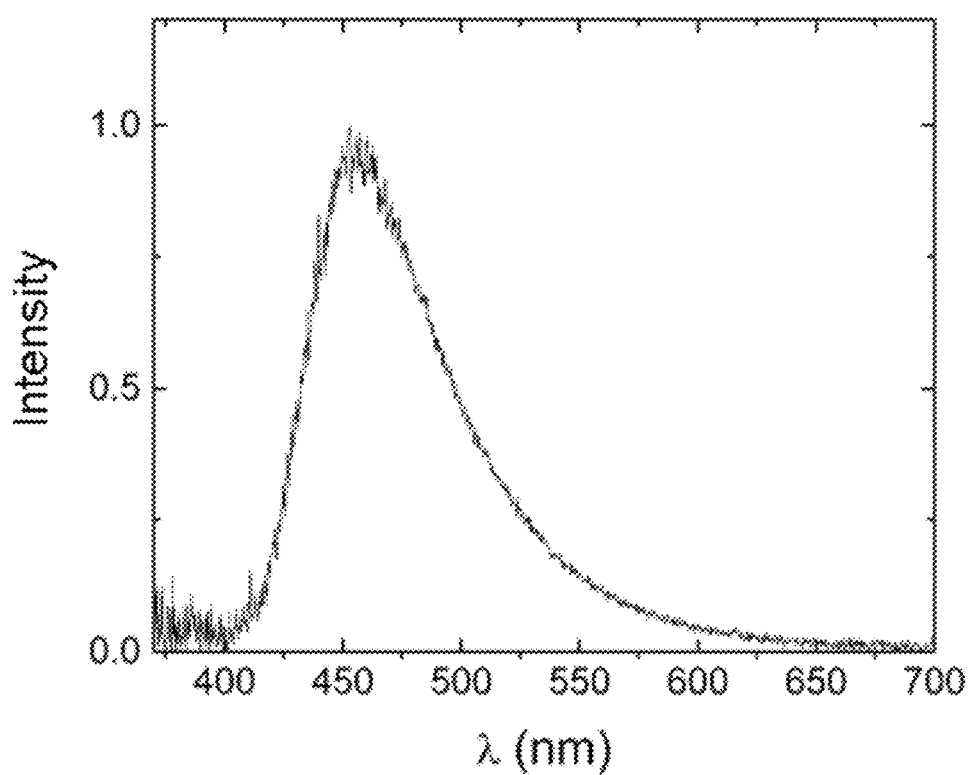
FIG. 21 is an electroluminescence spectrum of OLED component X2, on operation at 14 V.

The current density and luminance against the voltage are shown in FIG. 13. The power efficiency and current efficiency against the voltage are shown in FIG. 14. The external quantum efficiency against the current density is shown in FIG. 15. The electroluminescence spectrum on operation at 10 V of the OLED is shown in FIG. 16.

Example 11—OLED Component B

Molecule 1 was tested in an OLED component having the following construction: ITO/m-MTDATA/α-NPD/TCTA/CzSi/1(10%):DPEPO/DPEPO/TPBi/Liq/Al.

TABLE 2

| Component data for component B. | |
|---|---|
| Power efficiency | 7.7 lm/W |
| Current efficiency | 13.8 cd/A |
| CIE | CIEx: 0.16 |
| | CIEy: 0.17 |
| | @ 14 V |
| External quantum yield (EQE) | 10.1% |

Example 12

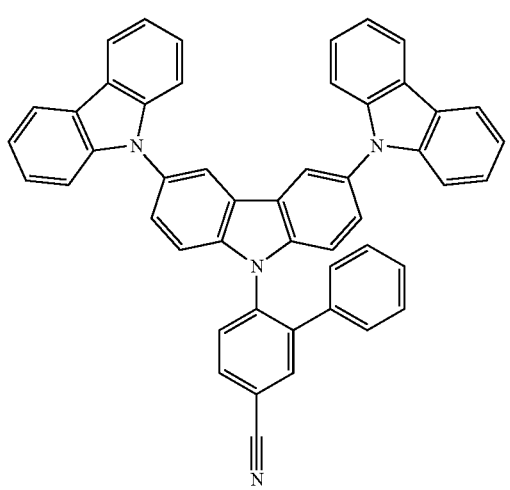

19

The film emission of 19 (10% in PMMA) was measured. The emission maximum is at 407 nm. The photoluminescence quantum yield (PLQY) is 30%.

Example 13

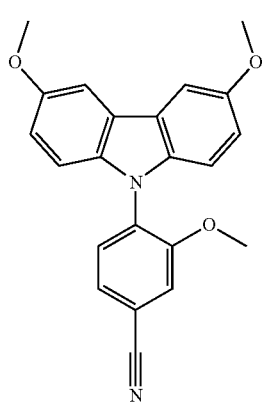

20

The film emission of 20 (10% in PMMA) was measured. The emission maximum is at 440 nm. The photoluminescence quantum yield (PLQY) is 50%.

Example 14

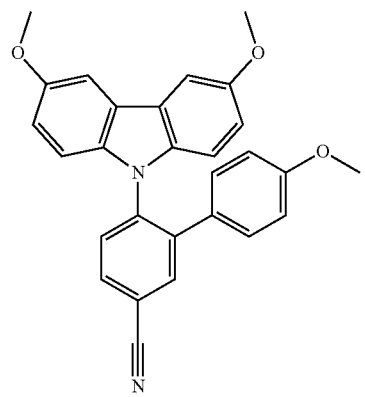

21

The film emission of 21 (10% in PMMA) was measured. The emission maximum is at 442 nm. The photoluminescence quantum yield (PLQY) is 52%.

Example 15

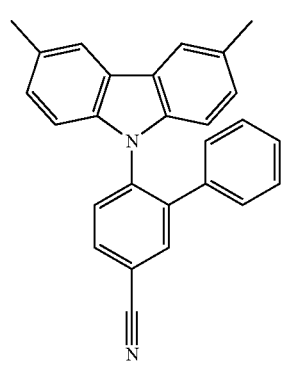

22

The film emission of 22 (10% in PMMA) was measured. The emission maximum is at 408 nm. The photoluminescence quantum yield (PLQY) is 41%.

Example 16

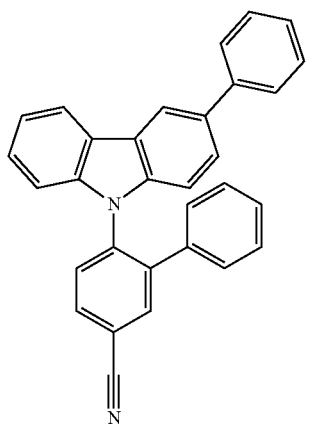

23

The film emission of 23 (10% in PMMA) was measured. The emission maximum is at 399 nm. The photoluminescence quantum yield (PLQY) is 31%.

Example 17

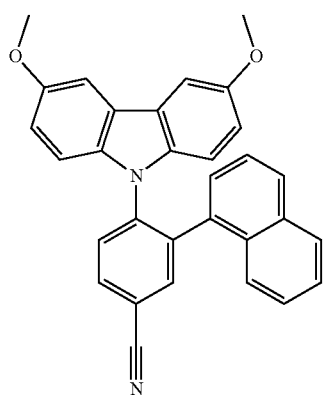

24

The film emission of 24 (10% in PMMA) was measured. The emission maximum is at 441 nm. The photoluminescence quantum yield (PLQY) is 32%. The full width at half maximum (FWHM) is 91 nm.

Example 18

25

The film emission of 25 (10% in PMMA) can be seen in FIG. F9. The emission maximum is at 474 nm. The photoluminescence quantum yield (PLQY) is 52%.

Example 19

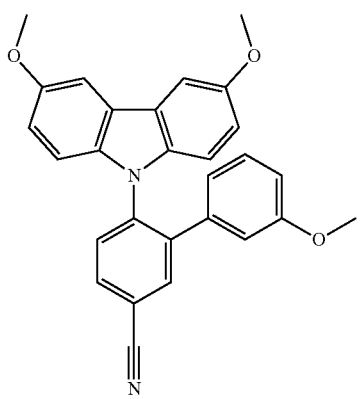

26

The film emission of 26 (10% in PMMA) was measured. The emission maximum is at 448 nm. The photoluminescence quantum yield (PLQY) is 53%.

Example 20

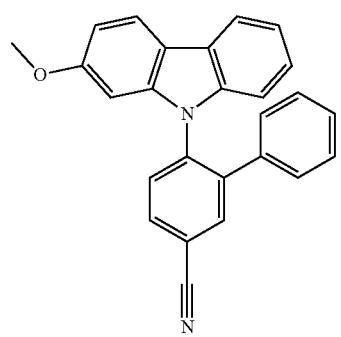

27

The film emission of 27 (10% in PMMA) was measured. The emission maximum is at 392 nm. The photoluminescence quantum yield (PLQY) is 30%.

Example 21

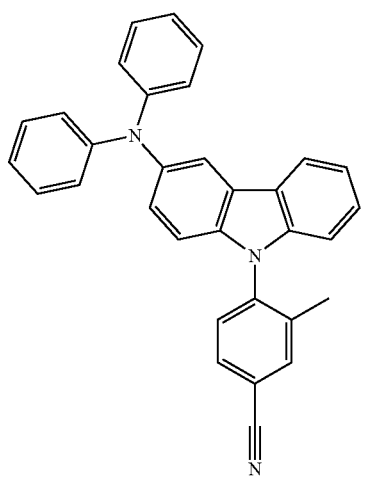

28

The film emission of 28 (10% in PMMA) was measured. The emission maximum is at 425 nm. The photoluminescence quantum yield (PLQY) is 16%.

Example 22

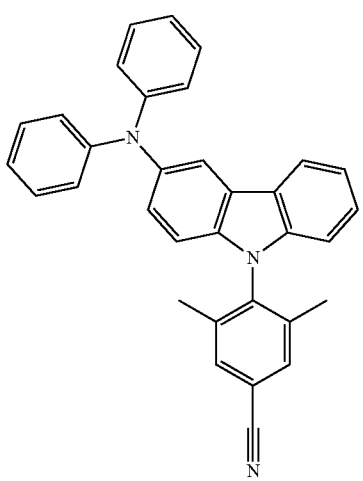

29

The film emission of 29 (10% in PMMA) was measured. The emission maximum is at 416 nm. The photoluminescence quantum yield (PLQY) is 13%.

Example 23

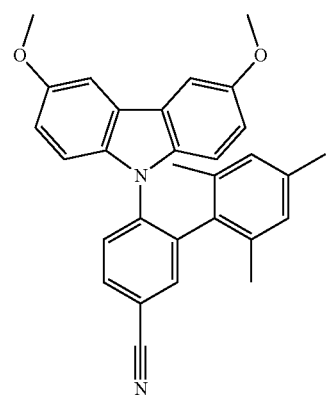

30

The film emission of 30 (10% in PMMA) was measured. The emission maximum is at 433 nm. The photoluminescence quantum yield (PLQY) is 34%.

Example 24

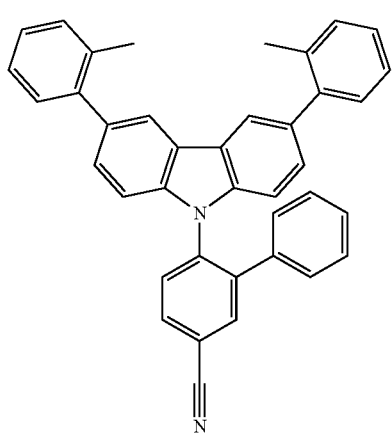

The film emission of 31 (10% in PMMA) was measured. The emission maximum is at 397 nm. The photoluminescence quantum yield (PLQY) is 33%.

Example 25

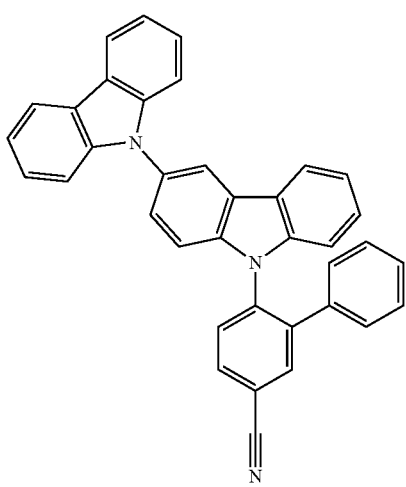

The film emission of 32 (10% in PMMA) was measured. The emission maximum is at 405 nm. The photoluminescence quantum yield (PLQY) is 37%.

Example 26

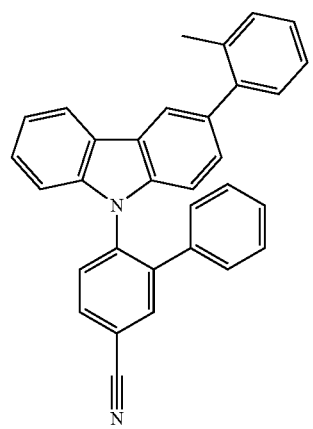

The film emission of 33 (10% in PMMA) was measured. The emission maximum is at 394 nm. The photoluminescence quantum yield (PLQY) is 37%.

Example 27

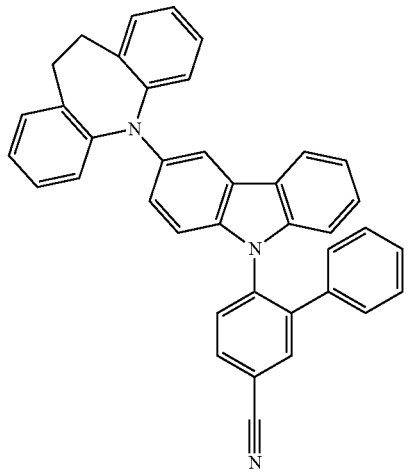

The film emission of 34 (10% in PMMA) was measured. The emission maximum is at 477 nm. The photoluminescence quantum yield (PLQY) is 33% and the full width at half maximum is 99 nm.

Molecule 5 is tested in an OLED component ("component X2") with the following construction (the fraction of the molecule of the invention in the emission layer is reported in percent by mass):

| Layer | Thickness | |
|---|---|---|
| 10 | 100 nm | Al |
| 9 | 2 nm | Liq |
| 8 | 30 nm | TPBi |

| | | |
|---|---|---|
| 7 | 10 nm | DPEPO |
| 6 | 20 nm | 5 (20%): DPEPO |
| 5 | 10 nm | CzSi |
| 4 | 20 nm | TCTA |
| 3 | 70 nm | NPB |
| 2 | 20 nm | m-MTDATA |
| 1 | 120 nm | ITO |
| Power efficiency: | | 12.9 lm/W |
| Current efficiency: | | 27.5 cd/A |
| CIE: | | CIEx: 0.165 |
| | | CIEy: 0.169 |
| | | at 14 V |
| Maximum external quantum yield (EQE): | | 20.3% |
Further examples of organic molecules having a structure in accordance with formula I:
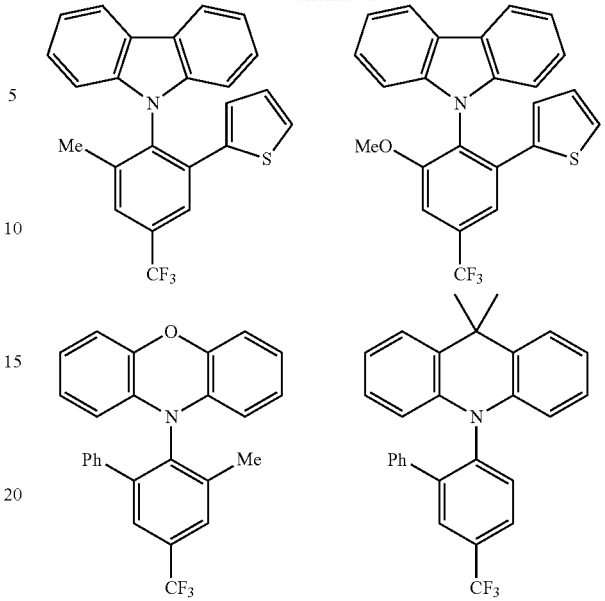

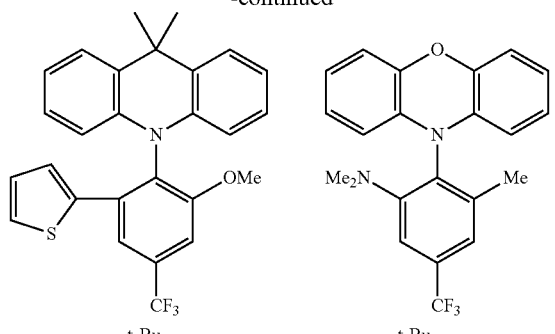
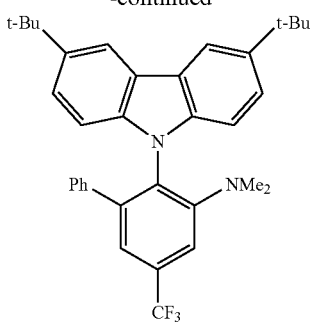
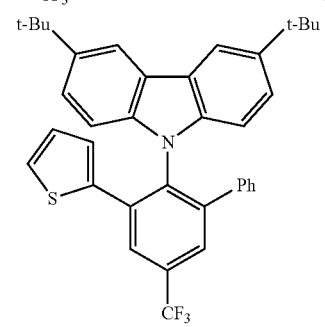
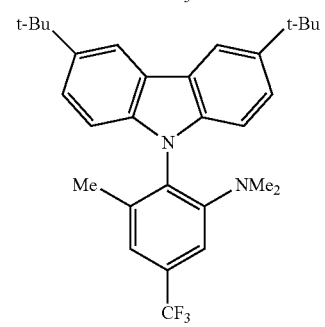
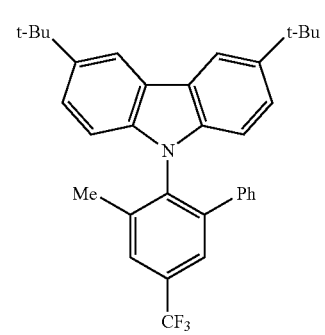
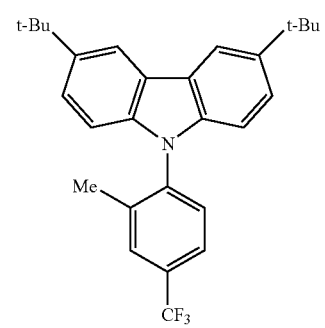

-continued
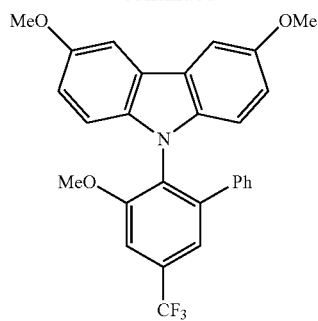
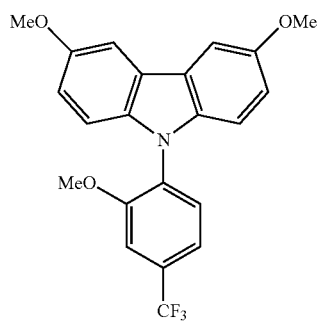
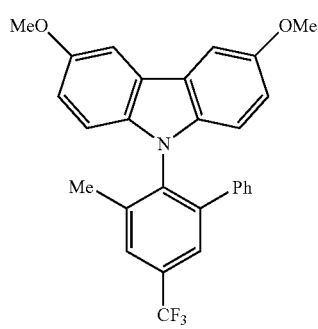
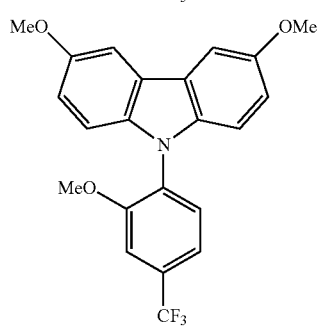
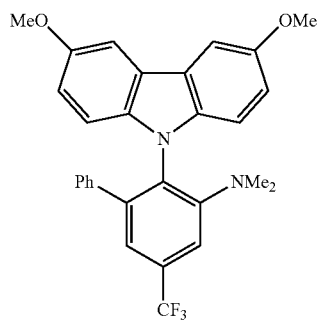
-continued
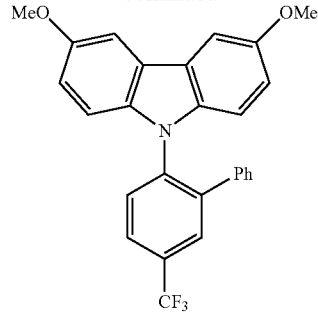
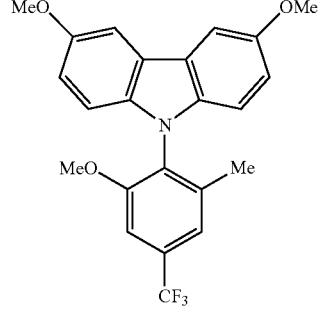
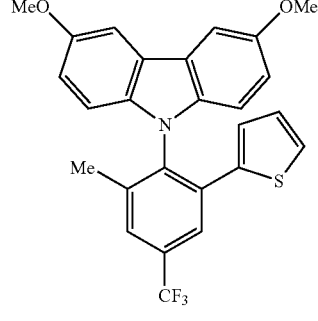
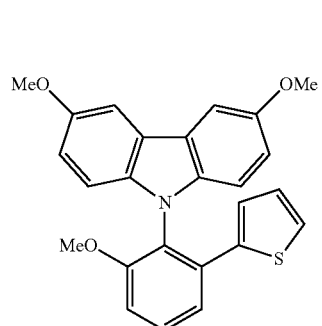
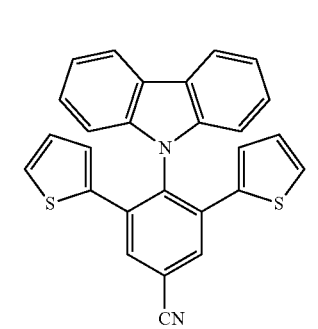

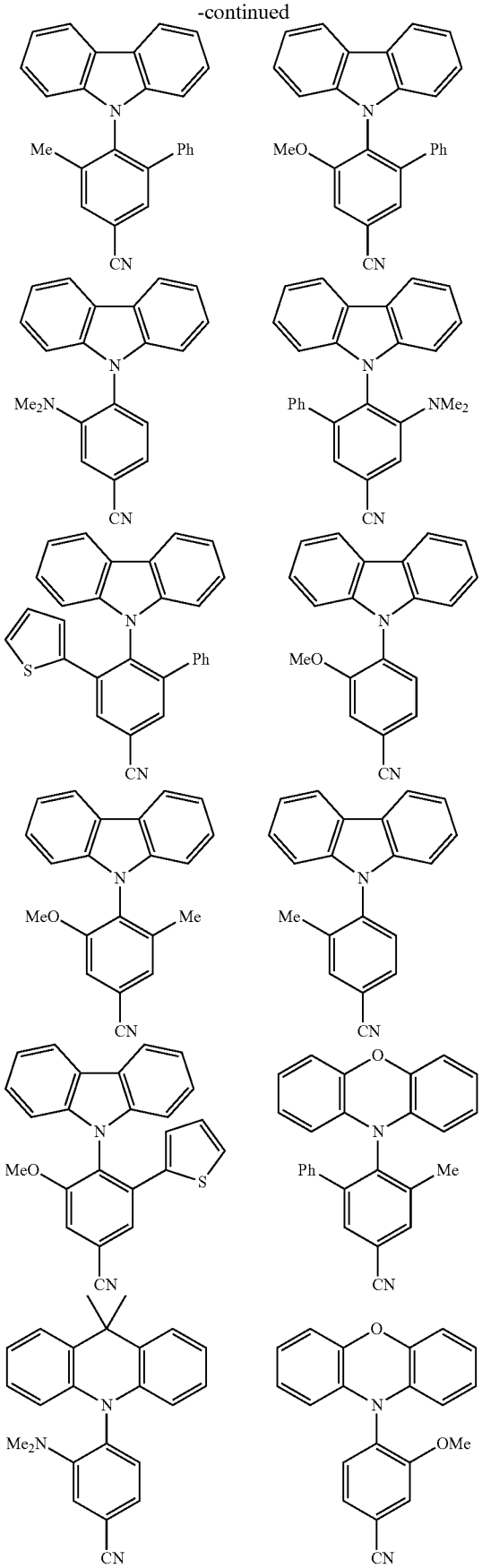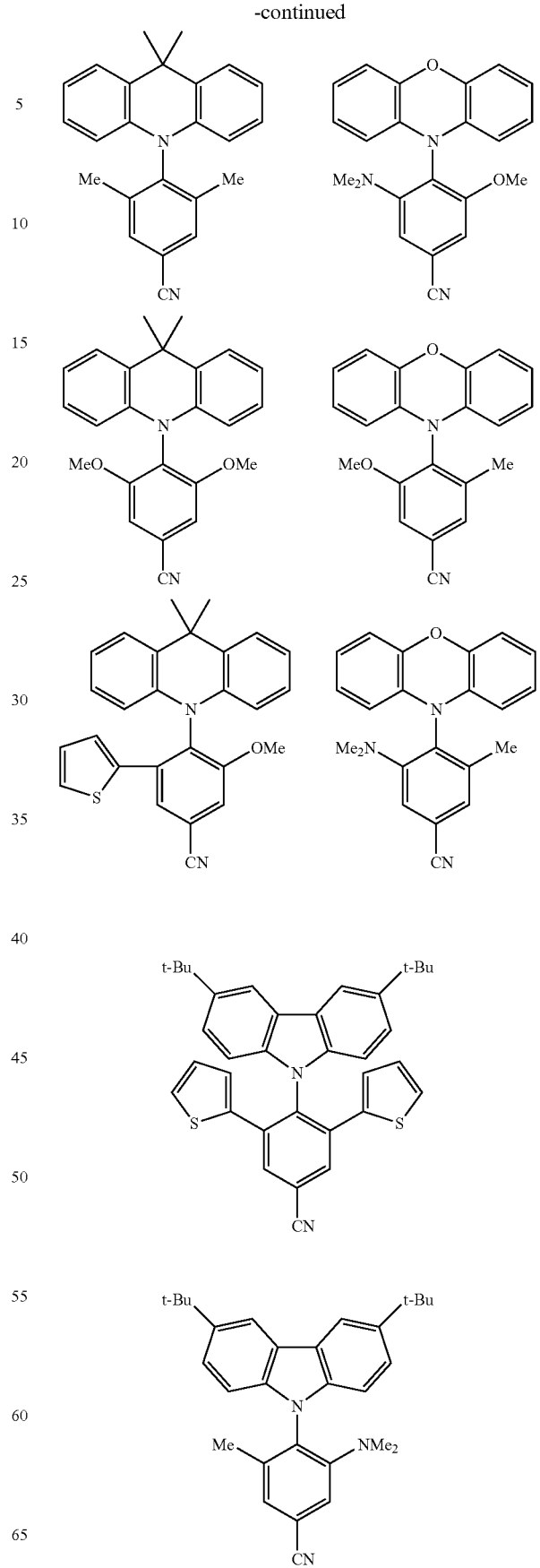

-continued
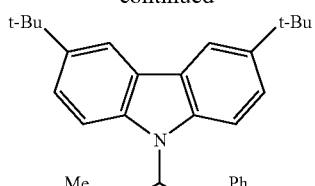
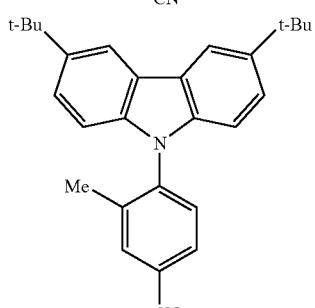
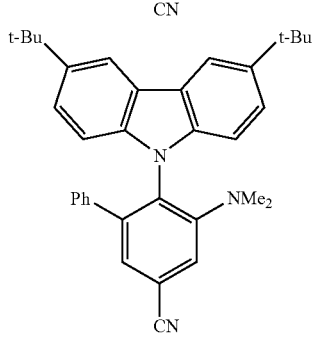
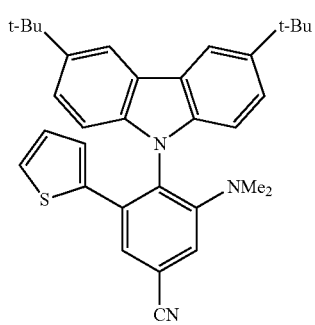
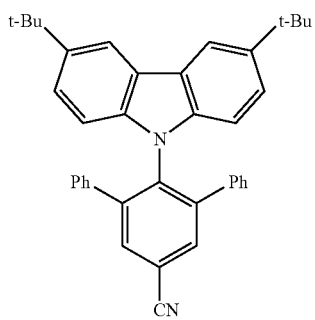
-continued
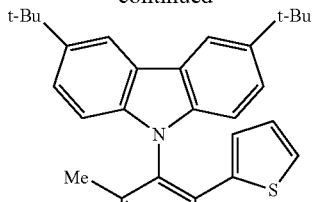
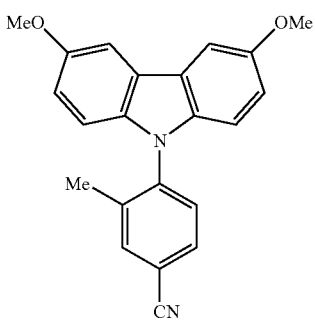
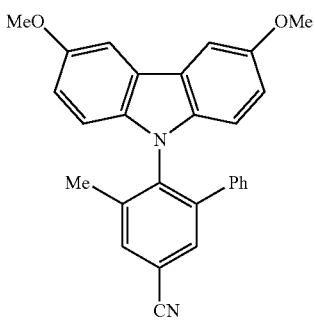

-continued
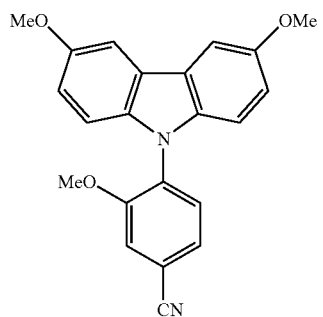
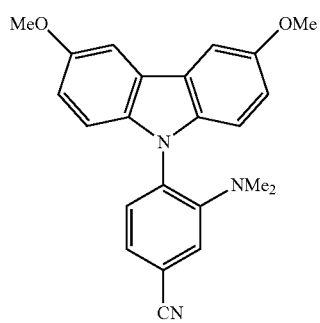
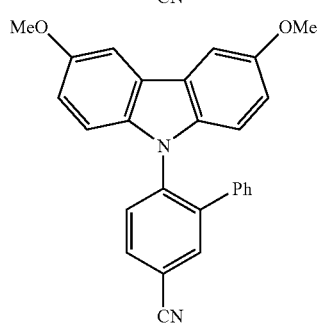
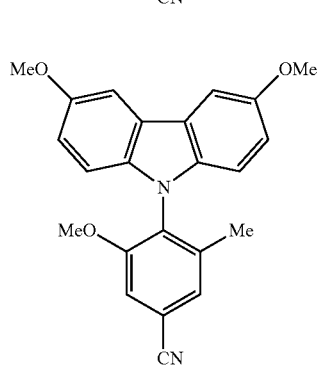
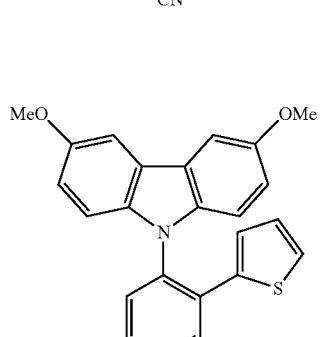
-continued
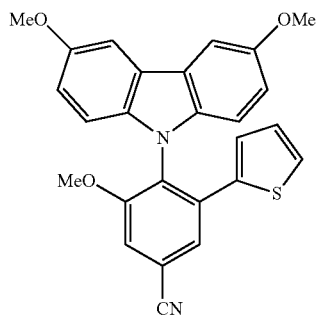
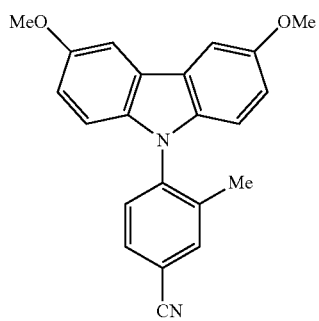
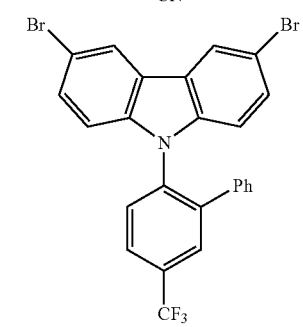
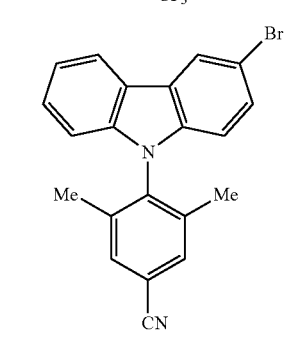
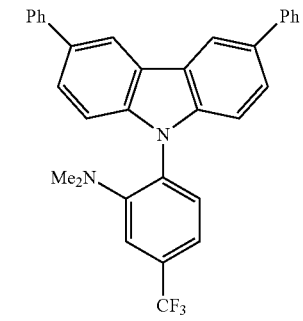

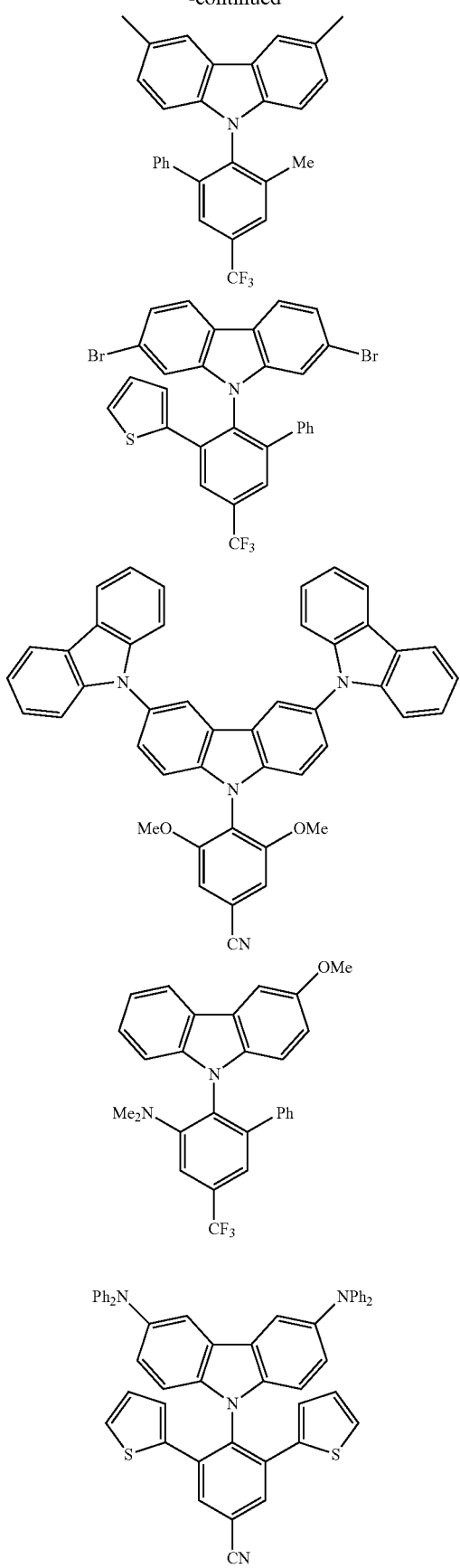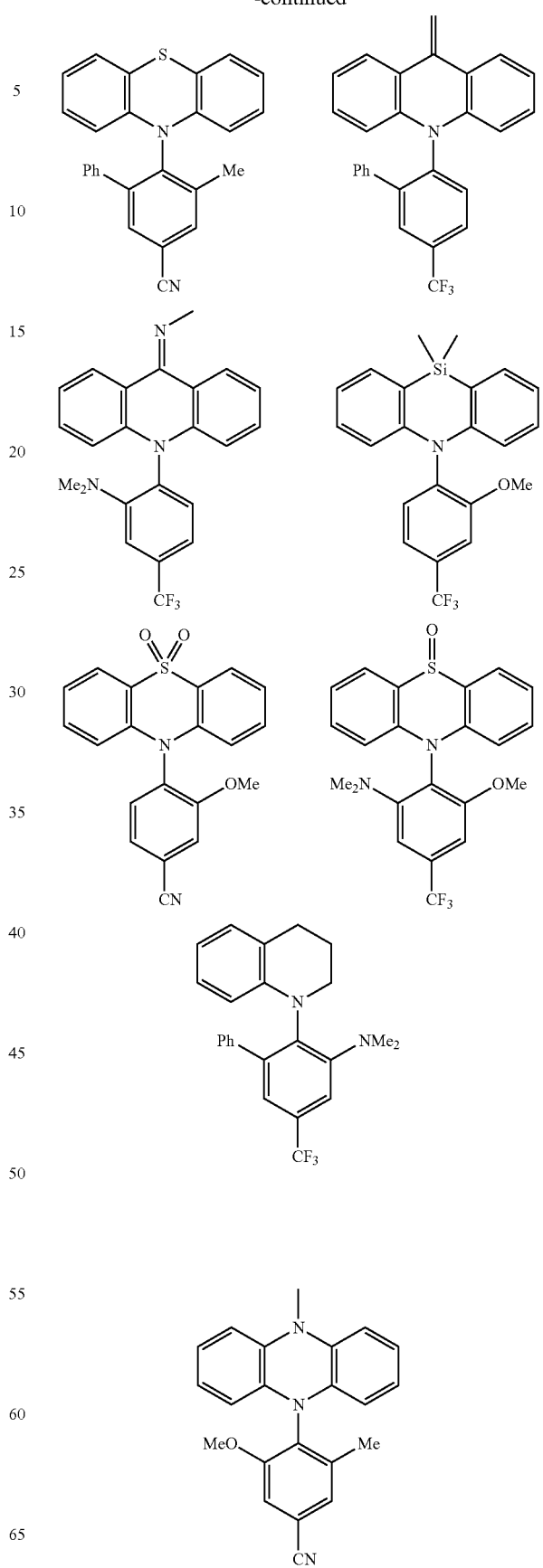

-continued

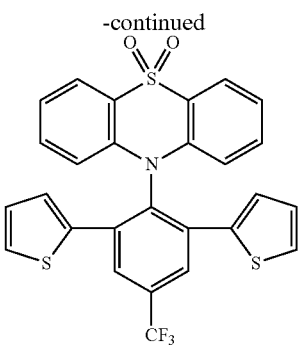

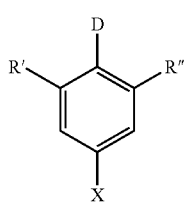

Although illustrative embodiments of the present invention have been described herein with reference to the accompanying drawings, it is to be understood that the invention is not limited to those precise embodiments, and that various other changes and modifications may be made by one skilled in the art without departing from the scope or spirit of the invention.

The invention claimed is:

1. An optoelectronic device comprising at least one light-emitting layer,
  wherein the at least one light emitting layer consists of an organic molecule comprising a structure of Formula I and a host material whose triplet (T1) and singlet (S1) energy levels are energetically higher than the triplet (T1) and singlet (S1) energy levels of the organic molecule,
  wherein the organic molecule is a luminescent emitter,
  wherein the at least one light emitting layer comprises no additional emitter material:

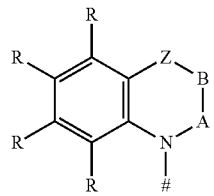

Formula I wherein
X=CN or CF$_3$;
D=a chemical unit comprising a structure of Formula 1-1:

Formula I-1 wherein
=an attachment point of the unit of Formula I-1 to a central phenyl ring of the structure of Formula I;
A and B=independently of one another are selected from the group consisting of CRR$^1$, CR, NR, and N, there being a single or double bond between A and B and a single or double bond between B and Z;
Z=a direct bond or a divalent organic bridge which is a substituted or unsubstituted C$_1$ to C$_9$-alkylene, C$_2$ to C$_8$-alkenylene, C$_2$ to C$_8$-alkynylene or arylene group or a combination thereof,
—C(Me)$_2$—, —C=CRR$^1$, C=NR, —NR—, —O—, —SiRR$^1$—, —S—, —S(O)—, —S(O)$_2$—, O-interrupted substituted or unsubstituted C$_1$ to C$_9$-alkylene, C$_2$ to C$_8$-alkenylene, C$_2$ to C$_8$-alkynylene or arylene group, phenyl units or substituted phenyl units;
where each R and R$^1$, identically or differently at each occurrence, is H, deuterium, azide (N$_3^-$), F, Cl, Br, I, N(R$^2$)$_2$, CN, CF$_3$, NO$_2$, OH, COOH, COOR$^2$, CO(NR$^2$)$^2$, Si(R$^2$)$_3$, B(OR$^2$)$_2$, C(=O) R$^2$, P(=O)(R$^2$)$_2$, S(=O)R$^2$, S(=O)$_2$R$^2$, OSO$_2$R$^2$, a linear alkyl, alkoxy or thioalkoxy group having 1 to 40 carbon atoms or a linear alkenyl or alkynyl group having 2 to 40 carbon atoms or a branched or cyclic alkyl, alkenyl, alkynyl, alkoxy or thioalkoxy group having 3 to 40 carbon atoms, which in each case may be substituted by one or more radicals R$^2$, it being possible for one or more non-adjacent CH$_2$ groups to be replaced by R$^2$C=CR$^2$, C≡C, Si(R$^2$)$_2$, Ge(R$^2$)$_2$, Sn(R$^2$)$_2$, C=O, C=S, C=Se, C=NR$^2$, P(=O)(R$^2$), SO, SO$_2$, NR$^2$, O, S or CONR$^2$, and it being possible for one or more H atoms to be replaced by deuterium, F, Cl, Br, I, CN, CF$_3$ or NO$_2$, or is an aromatic hydrocarbon ring system having 6 to 60 aromatic ring atoms optionally substituted by one or more radicals R$^2$ or a heteroaromatic ring system having 5 to 60 aromatic ring atoms, or is an aryloxy or heteroaryloxy group having 5 to 60 aromatic ring atoms, wherein the aryloxy or the heteroaryloxy group is optionally substituted by one or more radicals R$^2$, or is a diarylamino group, diheteroarylamino group or arylheteroarylamino group having 10 to 40 aromatic ring atoms, wherein the diarylamino group, the diheteroarylamino group or the arylheteroarylamino is optionally substituted by one or more radicals R$^2$, or is a combination of these systems, or is a crosslinkable unit QE which may be crosslinked by acid-catalytic, thermal or UV crosslinking methods in the presence or absence of a photoinitiator or by microwave radiation; optionally two or more of these substituents R and R$^1$ may form with one another a mono-or polycyclic, aliphatic, aromatic and/or benzo-fused ring system, wherein, when any R combines to form a carbazole group bonded to Formula I-1, the carbazole group is bonded to Formula I-1 through the nitrogen atom of the carbazole group;

$R^2$, identically or differently at each occurrence, is H, deuterium, F, Cl, Br, I, $N(R^3)_2$, CN, $CF_3$, $NO_2$, OH, COOH, $COOR^3$, $CO(NR^3)_2$, $Si(R^3)_3$, $B(OR^3)_2$, C(=O)$R^3$, P(=O)$(R^3)_2$, S(=O)$R^3$, S(=O)$_2R^3$, $OSO_2R^3$, a linear alkyl, alkoxy or thioalkoxy group having 1 to 40 carbon atoms or a linear alkenyl or alkynyl group having 2 to 40 carbon atoms or a branched or cyclic alkyl, alkenyl, alkynyl, alkoxy or thioalkoxy group having 3 to 40 C atoms, which may be substituted in each case by one or more radicals $R^3$, it being possible for one or more non-adjacent $CH_2$ groups to be replaced by $R^3C=CR^3$, C≡C, $Si(R^3)_2$, $Ge(R^3)_2$, $Sn(R^3)_2$, C=O, C=S, C=Se, C=$NR^3$, P(=O)$(R^3)$, SO, $SO_2$, $NR^3$, O, S or $CONR^3$, and it being possible for one or more H atoms to be replaced by deuterium, F, Cl, Br, I, CN, $CF_3$ or $NO_2$, or is an aromatic or heteroaromatic ring system having 5 to 60 aromatic ring atoms, wherein the aromatic or the heteroaromatic ring system is optionally substituted in each case by one or more radicals $R^3$, or is an aryloxy or heteroaryloxy group having 5 to 60 aromatic ring atoms, wherein the aryloxy or the heteroaryloxy group is optionally substituted by one or more radicals $R^3$, or is a diarylamino group, diheteroarylamino group or arylheteroarylamino group having 10 to 40 aromatic ring atoms, wherein the diarylamino group, the diheteroarylamino group or the arylheteroarylamino is optionally substituted by one or more radicals $R^3$, or is a combination of these systems; where optionally two or more of these substituents $R^2$ form with one another a mono- or polycyclic, aliphatic, aromatic and/or benzo-fused ring system;

$R^3$, identically or differently at each occurrence, is H, deuterium, F, $CF_3$ or an aliphatic, aromatic and/or heteroaromatic radical having 1 to 20 C atoms, in which also one or more H atoms may be replaced by F or $CF_3$; where optionally two or more substituents $R^3$ form with one another a mono- or polycyclic, aliphatic ring system;

R'=selected from the group consisting of H, N $(R^4)_2$, $OR^4$, thiophene, a linear alkyl or alkoxy group having 1 to 40 C atoms and a branched or cyclic alkyl or alkoxy group having 3 to 40 carbon atoms, it being possible for this group to be substituted in each case by one or more radicals $R^4$, and an aromatic hydrocarbon ring system having 6 to 60 aromatic ring atoms, wherein the aromatic ring system is optionally substituted in each case by one or more radicals $R^4$;

R"=selected from the group consisting of $N(R^4)_2$, $OR^4$, thiophene, a linear alkyl or alkoxy group having 1 to 40 C atoms and a branched or cyclic alkyl or alkoxy group having 3 to 40 carbon atoms, it being possible for this group to be substituted in each case by one or more radicals $R^4$, and an aromatic hydrocarbon ring system having 6 to 60 aromatic ring atoms, wherein the aromatic ring system is optionally substituted by one or more radicals $R^4$:

$R^4$, identically or differently at each occurrence, is H, deuterium, $N(R^5)_2$, $Si(R^5)_3$, a linear alkyl, alkoxy or thioalkoxy group having 1 to 40 carbon atoms or a branched or cyclic alkyl, alkoxy or thioalkoxy group having 3 to 40 carbon atoms, it being possible for this group to be substituted in each case by one or more radicals $R^5$, or is an aromatic or heteroaromatic ring system having 5 to 60 aromatic ring atoms, wherein the aromatic or the heteroaromatic ring system is optionally substituted in each case by one or more radicals $R^5$, or is an aryloxy or heteroaryloxy group having 5 to 60 aromatic ring atoms, wherein the aryloxy or the heteroaryloxy group is optionally substituted by one or more radicals $R^5$, or is a diarylamino group, diheteroarylamino group or arylheteroarylamino group having 10 to 40 aromatic ring atoms wherein the diarylamino group, the diheteroarylamino group or the arylheteroarylamino is optionally substituted by one or more radicals $R^5$, or is a combination of these systems; where optionally two or more of these substituents $R^5$ may also form with one another a mono- or polycyclic, aliphatic, aromatic and/or benzo-fused ring system; and $R^5$, identically or differently at each occurrence, is H, deuterium or an aliphatic, aromatic and/or heteroaromatic radical having 1 to 20 carbon atoms; where optionally two or more substituents $R^5$ may also form with one another a mono- or polycyclic, aliphatic ring system.

2. The optoelectronic device according to claim 1, wherein the optoelectronic device is an organic light-emitting diode, a light-emitting electrochemical cell, an organic light-emitting sensor, an organic diode, an organic solar cell, an organic transistor, an organic field-effect transistor, an organic laser or a down-conversion element.

3. The optoelectronic device according to claim 2, wherein a proportion of the organic molecule in an emission layer in the optoelectronic device is 1 vol. % to 99 vol. %.

4. The optoelectronic device according to claim 2, wherein a proportion of the organic molecule in an emission layer in the optoelectronic device is 5 vol. % to 80 vol. %.

5. The optoelectronic device according to claim 1, comprising:
a substrate;
an anode;
a cathode, wherein the anode or the cathode is applied to the substrate; and
at least one light-emitting layer disposed between the anode and the cathode and which comprises the organic molecule.

6. The optoelectronic device according to claim 2, comprising:
a substrate;
an anode;
a cathode, wherein the anode or the cathode is applied to the substrate; and
at least one light-emitting layer disposed between the anode and the cathode and which comprises the organic molecule.

7. The optoelectronic device according to claim 1, wherein for the organic molecule the structure of Formula 1-1 has a structure of Formula II:

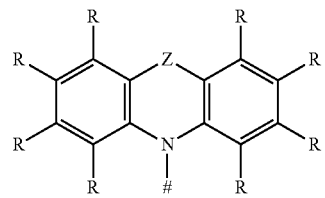

Formula II where #, Z and R have the aforestated meanings.

8. The optoelectronic device according to claim 1, wherein for the organic molecule the structure of Formula I-1 has a structure of Formula III:

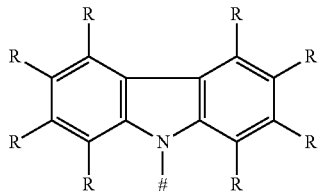

Formula III where # and R have the aforestated meanings.

9. The optoelectronic device according to claim 1, wherein for the organic molecule X of the structure of Formula I is CN.

10. The optoelectronic device according to claim 1, wherein for the organic molecule X of the structure of Formula I is $CF_3$.

11. The optoelectronic device according to claim 1, wherein for the organic molecule the radical R' of the structure of Formula I is a hydrogen atom.

12. The optoelectronic device according to claim 1, wherein for the organic molecule:

R'=selected from the group consisting of H, $N(R^4)_2$, $OR^4$, a linear alkyl or alkoxy group having 1 to 40 C atoms and a branched or cyclic alkyl or alkoxy group having 3 to 40 carbon atoms, it being possible for this group to be substituted in each case by one or more radicals $R^4$, and an aromatic hydrocarbon ring system having 6 to 60 aromatic ring atoms, wherein the aromatic ring system is optionally substituted in each case by one or more radicals $R^4$;

R"=selected from the group consisting of $N(R^4)_2$, $OR^4$, a linear alkyl or alkoxy group having 1 to 40 C atoms and a branched or cyclic alkyl or alkoxy group having 3 to 40 carbon atoms, it being possible for this group to be substituted in each case by one or more radicals $R^4$, and-an aromatic hydrocarbon ring system having 6 to 60 aromatic ring atoms, wherein the aromatic ring system is optionally substituted by one or more radicals $R^4$.

13. The optoelectronic device according to claim 12, comprising:
a substrate;
an anode;
a cathode, wherein the anode or the cathode is applied to the substrate; and
at least one light-emitting layer disposed between the anode and the cathode and which comprises the organic molecule.

* * * * *